United States Patent [19]
Hossack et al.

[11] Patent Number: 6,005,827
[45] Date of Patent: *Dec. 21, 1999

[54] ULTRASONIC HARMONIC IMAGING SYSTEM AND METHOD

[75] Inventors: John A. Hossack, Palo Alto; Christopher R. Cole, Redwood City; Jian-Hua Mo, Milpitas, all of Calif.

[73] Assignee: Acuson Corporation, Mountain View, Calif.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/893,288

[22] Filed: Jul. 15, 1997

Related U.S. Application Data

[63] Continuation-in-part of application No. 08/642,528, May 3, 1996, Pat. No. 5,740,128, which is a continuation-in-part of application No. 08/397,833, Mar. 2, 1995, Pat. No. 5,608,690.

[51] Int. Cl.⁶ .................................................... G01S 15/89
[52] U.S. Cl. .................................................................. 367/7
[58] Field of Search ................................. 367/7, 11, 138; 600/447, 444, 458

[56] References Cited

U.S. PATENT DOCUMENTS

| | | | |
|---|---|---|---|
| 4,702,258 | 10/1987 | Nicolas et al. | 600/443 |
| 4,712,037 | 12/1987 | Verbeek et al. | |
| 4,714,846 | 12/1987 | Pesque et al. | 310/317 |
| 5,040,537 | 8/1991 | Katakura . | |
| 5,111,823 | 5/1992 | Cohen . | |
| 5,113,706 | 5/1992 | Pittaro . | |
| 5,115,809 | 5/1992 | Saitoh et al. | |
| 5,190,766 | 3/1993 | Ishihara . | |
| 5,195,520 | 3/1993 | Schlief et al. | |
| 5,215,680 | 6/1993 | D'Arrigo . | |
| 5,219,401 | 6/1993 | Cathignol et al. | |
| 5,255,683 | 10/1993 | Monaghan . | |
| 5,358,466 | 10/1994 | Aida et al. | |
| 5,380,411 | 1/1995 | Schlief . | |
| 5,410,205 | 4/1995 | Gururaja . | |
| 5,410,516 | 4/1995 | Uhlendorf et al. | |

(List continued on next page.)

FOREIGN PATENT DOCUMENTS

| | | |
|---|---|---|
| 0 357 164 | 3/1990 | European Pat. Off. . |
| 0 770 352 A1 | 5/1997 | European Pat. Off. . |
| WO 98/20361 | 5/1998 | WIPO . |

OTHER PUBLICATIONS

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1995.

Marc Gensane, "Bubble population measurements with a parametric array." J. Acoustical Society of America, 95 (6), Jun. 1994.

(List continued on next page.)

Primary Examiner—Daniel T. Pihulic
Attorney, Agent, or Firm—Brinks Hofer Gilson & Lione

[57] ABSTRACT

A method for imaging a target includes the steps of transmitting ultrasonic energy at a fundamental frequency and receiving reflected ultrasonic energy at a harmonic of the fundamental frequency. The ultrasonic energy is transmitted in power bursts, each having a respective envelope shape, wherein the envelope shapes rise gradually to a respective maximum value and fall gradually from the respective maximum value. Ultrasonic energy in the transmit beam is focused in an elongated high power region, as for example by means of a line focus.

74 Claims, 10 Drawing Sheets

U.S. PATENT DOCUMENTS

| | | |
|---|---|---|
| 5,417,214 | 5/1995 | Roberts et al. . |
| 5,425,366 | 6/1995 | Reinhardt et al. . |
| 5,433,207 | 7/1995 | Pretlow, III . |
| 5,438,554 | 8/1995 | Seyed-Bolorforosh et al. . |
| 5,456,255 | 10/1995 | Abe et al. . |
| 5,456,257 | 10/1995 | Johnson et al. . |
| 5,469,849 | 11/1995 | Sasaki et al. . |
| 5,479,926 | 1/1996 | Ustuner et al. . |
| 5,482,046 | 1/1996 | Deitrich . |
| 5,523,058 | 6/1996 | Umemura et al. . |
| 5,526,816 | 6/1996 | Arditi . |
| 5,540,909 | 7/1996 | Schutt ................................... 424/9.52 |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,675,554 | 10/1997 | Cole et al. . |
| 5,678,554 | 10/1997 | Hossack et al. . |
| 5,696,737 | 12/1997 | Hossack et al. . |
| 5,724,976 | 3/1998 | Mine et al. . |
| 5,740,128 | 4/1998 | Hossack et al. . |

OTHER PUBLICATIONS

Ken Ishihara, et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

V.L. Newhouse, et al., "Bubble size measurements using the nonlinear mixing of two frequencies." J. Acoustical Society of America, 75 (5), May 1984.

"Small Spheres Lead to Big Ideas." Research News, Science vol. 267, Jan. 20, 1995.

Abstracts Journal of the American Society of Echocardiography, vol. 8, No. 3 pp. 345–346, 355, 358–364.

Deborah J. Rubens, MD, et al., "Sonoelasticity Imaging of Prostate Cancer: In Vitro Results." Radiology, vol. 195, No. 2, 1995.

B. Schrope, et al., "Simulated Capillary Blood Flow Measurement Using a Nonlinear Ultrasonic Contrast Agent." Ultrasonic Imaging 14 (1992).

Fred Lee, Jr., MD, et al., "Sonoelasticity Imaging: Results in in Vitro Tissue Specimens." Radiology, vol. 181, No. 1 (1991).

Kevin J. Parker, PhD., et al ., "Sonoelasticity of Organs: Shear Waves Ring A Bell." J. Ultrasound Med., 11 (1992).

William Armstrong, M.D., et al., "Position Paper on Contrast Echocardiography." American Society of Echocardiography, draft 1, Jun. 6, 1994.

K.J. Parker, et al., "Tissue Response to Mechanical Vibrations for 'Sonoelasticity Imaging'." Ultrasound in Med. and Biol., vol. 16, No. 3, (1990).

Robert M. Lerner, et al., "'Sonoelasticity' Images Derived from Ultrasound Signals in Mechanically Vibrated Tissues." Ultrasound in Med. and Biol., vol. 16, No. 3 (1990).

excerpt from Ultrasonics: Fundamentals and Applications (1992), pp. 380–393, 363–365.

J.A. Hossack, et al., "Improving Transducer Performance Using Multiple Active Layers." SPIE vol. 1733 (1992).

Volkmar Uhlendorf, et al., "Nonlinear Acoustical Response of Coated Microbubbles in Diagnostic Ultrasound." IEEE 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." IEEE 1980 Ultrasonics Symposium.

"HP Ultrasound Technologies—Viability." About HP Ultrasound Imaging, WWW document, 1997.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology." American College of Cardiology, $45^{th}$ Annual Scientific Session, Mar. 24–27, 1996 pp. 21A, 63A, 239–240A.

Yang–Sub Lee, et al., "Time–Domain Modeling of Pulsed Finite–Amplitude Sound Beams." J. Acoustical Society of America, 97 (2), Feb. 1995.

Michalakis A. Averkiou, et al., "Self–Demodulation of Amplitude and Frequency–Modulated Pulses in a Thermoviscous Fluid." J. Acoustical Society of America, 94 (5), Nov. 1993.

IEEE Transactions on Ultrasonics, Ferroelectrics, and Frequency Control, vol. 44, No. 1, Jan. 1997, pp. 125–139.

1980 IEEE Ultrasonics Symposium, pp. 757–762.

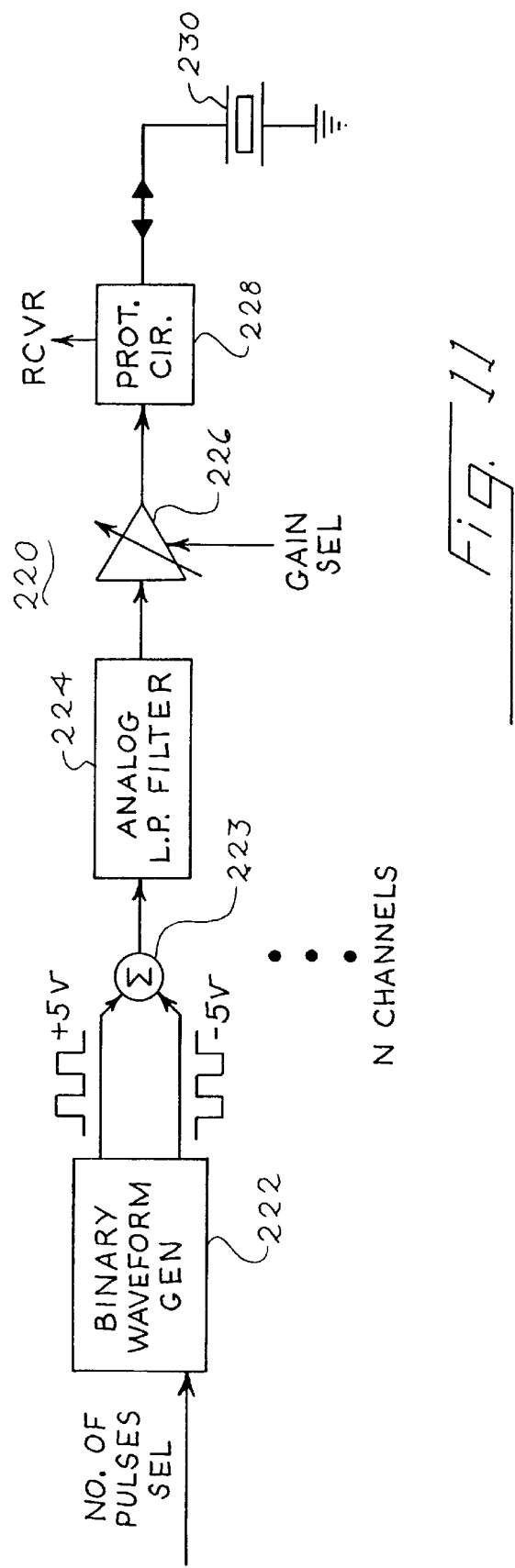
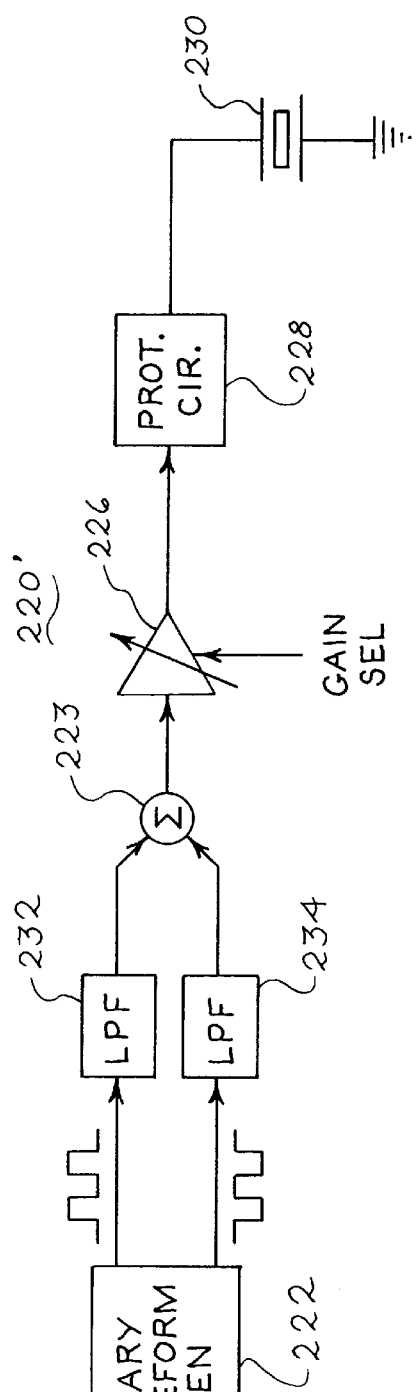
Fig. 11
Fig. 11a

ULTRASONIC HARMONIC IMAGING SYSTEM AND METHOD

CROSS REFERENCE TO RELATED APPLICATION

This application is a continuation-in-part of U.S. patent application Ser. No. 08/642,528, filed May 3, 1996, now U.S. Pat. No. 5,740,128 which is in turn a continuation-in-part of U.S. patent application Ser. No. 08/397,833, filed Mar. 2, 1995, now U.S. Pat. No. 5,608,690. These co-pending applications are hereby incorporated by reference in their entirety.

BACKGROUND OF THE INVENTION

This invention relates to ultrasound imaging systems, and in particular to improved methods for imaging nonlinear contrast agents with such systems.

Nonlinear contrast agents are described for example by V. Uhlendorf, et al., in "Nonlinear Acoustical Response of Coated Microbubbles in Diagnostic Ultrasound" (1995 Ultrasonic Symposium, pp. 1559–1562). Such agents possess a fundamental resonant frequency. When they are insonified with high intensity ultrasonic energy at this fundamental frequency, they radiate ultrasonic frequency at a harmonic of the fundamental frequency. Such contrast agents are often used to highlight regions containing blood loaded with the contrast agent. For example, in the case of a blood-filled chamber of the heart, the borders of the chamber can be distinguished more easily when contrast agent is used. Since the contrast agent generates harmonic ultrasound energy, echoes from tissue (containing no contrast agent) at the fundamental frequency may be eliminated by filtering at the receive beamformer.

Typically, such agents are used with an imaging system having a transmit beamformer that transmits ultrasonic energy at the fundamental frequency and a receive beamformer responsive to the harmonic. In order to image the contrast agent clearly, it is known to reduce energy at the harmonic in the transmit beam, and to reduce sensitivity of the receive beamformer to energy at the fundamental.

In the past, this has been done by using a burst of square or sine waves to form the transmit beam, and by using appropriate band pass or high pass filters in the receive beamformer. Though a large pulse count reduces energy at the harmonic, it reduces time resolution of the pulse, and therefore spatial resolution of the resulting image.

The present invention is directed to further improvements that enhance the imaging of such nonlinear contrast agents.

SUMMARY OF THE INVENTION

This invention relates to improvements to a method for imaging a target, which method comprises the steps of (a) transmitting ultrasonic energy at a fundamental frequency and (b) receiving reflected ultrasonic energy at a harmonic of the fundamental frequency.

According to a first aspect of this invention, the transmitting step includes the step of transmitting ultrasonic energy in power bursts, each power burst comprising a respective envelope shape, the envelope shapes rising gradually to a respective maximum value and falling gradually from the respective maximum value. This arrangement can reduce harmonic energy in the power burst.

According to a second aspect of this invention, the transmitting step includes the step of generating a transmit waveform and filtering the transmit waveform with a filter adapted to reduce ultrasonic energy in the transmit waveform at the harmonic of the fundamental frequency to at least −30 dB with respect to the fundamental frequency.

According to a third aspect of this invention, the transmitting step includes the step of generating a transmit waveform with a programmable waveform generator such that ultrasonic power in the transmit waveform at the harmonic of the fundamental frequency is reduced by at least −30 dB with respect to ultrasonic power in the transmit waveform at the fundamental frequency.

According to a fourth aspect of this invention, the transmitting step includes the step of focusing ultrasonic energy in a transmit beam having a line focus.

According to a fifth aspect of this invention, the transmitting step includes the step of focusing ultrasonic energy in a transmit beam having an elongated high power region by focusing at least first selected frequency components from at least a first plurality of transducer elements at a first range and focusing at least second frequency components from at least a second plurality of transducer elements at a second range.

Other aspects of the invention relate to the use of switched filters in the transmitting step.

BRIEF DESCRIPTION OF THE DRAWINGS

FIGS. 10, 11, and 11a are block diagrams of portions of transmit beamformers that incorporate preferred embodiments of this invention.

FIG. 12 is a waveform diagram illustrating operation of the beamformers of FIGS. 10–11a.

FIGS. 13–16 are graphs illustrating the temporal and frequency characteristics of waveforms produced by the beamformers of FIGS. 10–11a.

FIG. 17 is a graph illustrating a filter transfer function suitable for use in the beamformers of FIGS. 10–11a.

DETAILED DESCRIPTION OF THE PRESENTLY PREFERRED EMBODIMENTS

Figure 1:
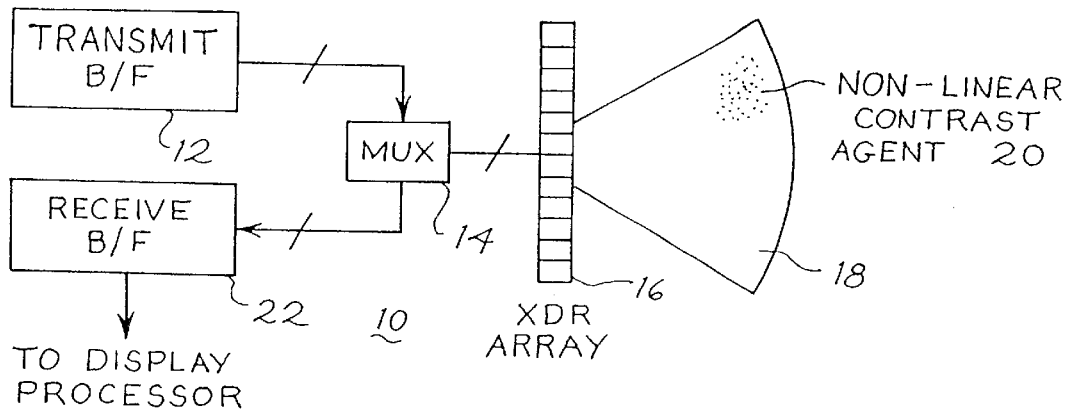
FIG. 1 is a block diagram of an ultrasonic imaging system suitable for use with the method of this invention.

The preferred embodiments described below are designed to reduce harmonic energy in the transmitted beam, and to provide an improved spatial distribution of fundamental energy in the transmitted beam. FIG. 1 shows generally an ultrasonic imaging system 10 which can be used to practice the method of this invention.

The system 10 includes a transmit beamformer 12 that supplies high voltage transmit waveforms via a multiplexer 14 to a transducer array 16. The transducer array 16, which can be any suitable type, generates an ultrasonic transmit beam in response to the transmit waveforms, and this transmit beam propagates outwardly through the subject 18 being imaged. In this case, the subject being imaged includes a nonlinear contrast agent 20, such as that described above. Any suitable contrast agent may be used, as long as it absorbs ultrasonic energy at a first frequency and radiates ultrasonic energy at a second frequency, different from the first frequency. In this example, the first frequency is referred to as the fundamental frequency, and the second frequency is a harmonic of the first frequency. As used herein, "harmonic" is intended broadly to include subharmonics and fractional harmonic energy (e.g. ½ or 3⁄2 of the fundamental), as well as higher harmonics (e.g. 2 or 3 times the fundamental).

Ultrasonic energy radiated by the nonlinear contrast agent 20 at the harmonic frequency is received by the transducer array 16, focused by the receive beamformer 22, and displayed as an image by a display processor (not shown). As described above, the receive beamformer 22 includes conventional filters to substantially prevent reflected ultrasonic energy at the fundamental frequency from being imaged.

Figure 2:
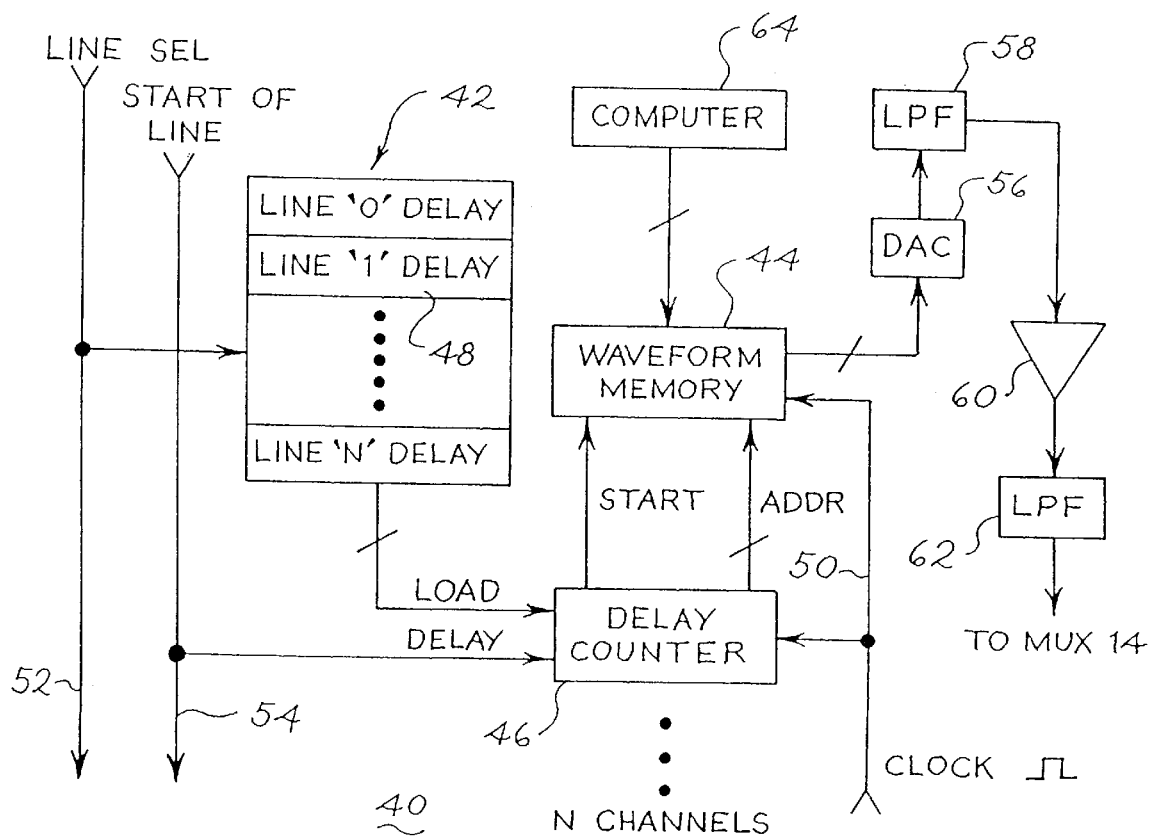
FIG. 2 is a block diagram of a transmit beamformer suitable for use in the system of FIG. 1.

Turning now to FIG. 2, this figure shows a block diagram of a first preferred embodiment 40 of the transmit beamformer of FIG. 1. As shown in FIG. 2, the transmit beamformer 40 includes N channels, one for each of the transducers of the transducer array 16 (FIG. 1). Each channel includes a delay memory 42, a waveform memory 44, and a delay counter 46 (FIG. 2). The delay memory 42 includes 256 words 48, one for each possible steering angle or ultrasound transmit scan line. Each word 48 of the delay memory 42 is set equal to a negative number equal to the number of clock cycles on the clock signal line 50 that elapse between a start of line signal on line 54 and the first non-zero value of the associated waveform. For simplicity, it is assumed that zero is defined as a word 48 having the most significant bit equal to one and all other bits equal to zero. Hence, the most significant bit becomes an enable signal for the waveform memory 44.

The waveform memory 44 in this embodiment stores a single waveform in digital form, which is used for all transmit scan lines. The waveform memory 44 can include for example 64 or 128 successive 8 bit words. The magnitude of each 8 bit word corresponds to the voltage amplitude at the respective position in the waveform. When the waveform memory 44 is read with a 40 MHz clock on the line 50, the resulting sequence of digital values defines a waveform approximately 1.6 to 3.2 microseconds in duration.

The delay memory 42 is not required, but it reduces memory requirements for the waveform memory 44. This is because the delay memory 42 eliminates the need to store a large number of leading zeros when the ultrasound line is steered at a large angle.

In use, each channel responds to a scan line selection signal on line 52 by loading the word 48 for the selected scan line into the delay counter 46. The delay counter 46 responds to a start of scan line signal on line 54 by incrementing the stored value with each cycle of the 40 MHz clock on line 50. When the counter 46 increments to zero, it enables the waveform memory 44. Subsequently generated values of the counter 46 (incrementing now from zero upwards) become address values for the waveform memory 44. As each word of the waveform memory 44 is addressed, the corresponding 8 bit word is read and applied to a digital to analog converter 56.

The analog output signal of the converter 56 is passed through a low pass filter such as a Bessel filter 58 to reduce sampling effects and then to an amplifier 60. The output of the amplifier 60 can be passed through an additional low pass filter 62 to improve harmonic rejection. The output of the low pass filter 62 is the transmit waveform discussed above that is applied to the respective transducer via the multiplexer 14 (FIG. 1). The low pass filters 58, 62 preferably provide a sharp cut-off with a low stop band level in order substantially to eliminate ultrasonic energy in the transmitted pulse at the harmonic frequency.

The transmit beamformer 40 utilizes values for the waveforms stored in the waveform memory 44 and the delays stored in the delay memory 42 that enhance insonification of the nonlinear contrast agent in the subject.

Figure 3:
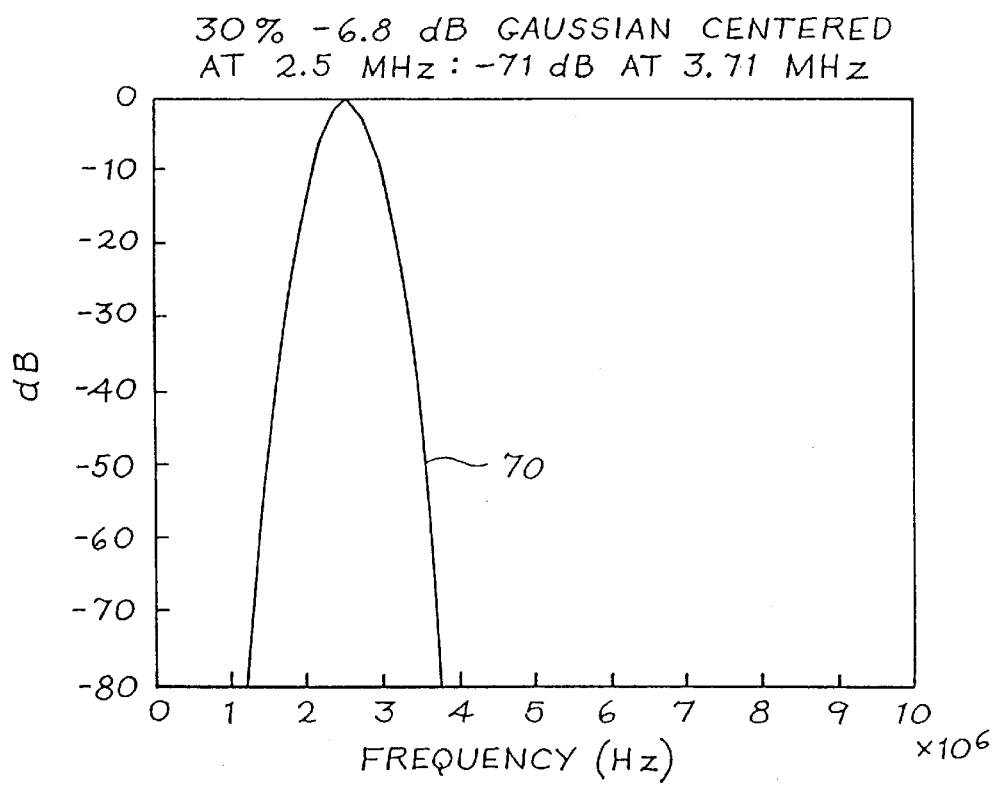
FIG. 3 is a graph of a Gaussian pulse in the frequency domain.

The waveform stored in the waveform memory 44 is shaped to suppress ultrasonic energy in a wide pass band centered at the harmonic frequency. For example, the spectrum of the desired pulse can be designed on a computer 64. FIG. 3 shows the frequency spectrum of one suitable pulse 70 which is centered at the fundamental frequency of 2.5 MHz and is generally Gaussian in shape. The particular Gaussian shape shown in FIG. 3 has an amplitude reduced by 71 dB at 3.71 MHz. The bandwidth of the pulse 70 is 30% of the center frequency, measured at points −6.8 dB with respect to the peak amplitude. Such a pulse will be referred to herein as a 30% BW Gaussian pulse. Note that the pulse 70 has substantially no energy at 5 MHz, the first harmonic of the fundamental frequency. This invention is not limited to use with Gaussian pulses, and a wide range of spectra can be used.

Figure 4:
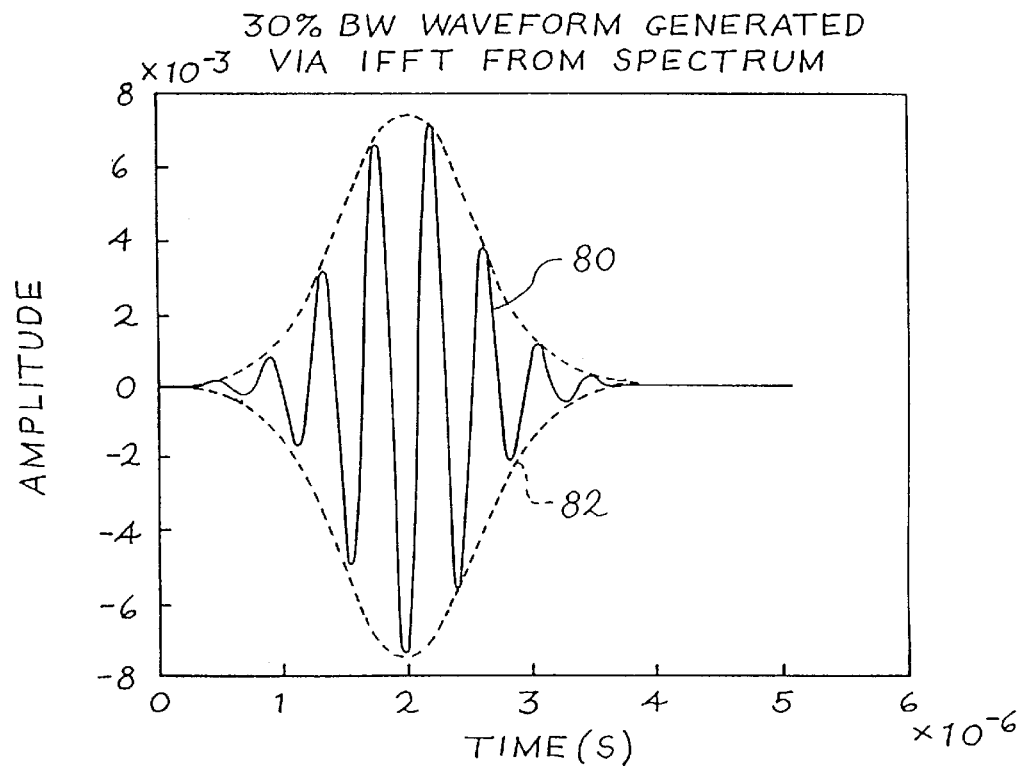
FIG. 4 is a graph of a waveform corresponding to the Gaussian pulse of FIG. 3 in the time domain.

Once the desired pulse has been designed, an inverse fast Fourier transform is then performed to generate the corresponding time domain waveform. FIG. 4 shows a waveform 80 which corresponds to the pulse 70 of FIG. 3. Note that the waveform 80 includes an oscillating component having a frequency of about 2.5 MHz. This oscillating component is shaped by an envelope 82. The envelope 82 rises gradually from zero amplitude to a maximum amplitude, and then falls gradually from the maximum amplitude back to zero amplitude. Thus, the envelope 82 is quite different from the envelope for a switched pulse train, which is substantially rectangular in shape. The gradually increasing and gradually decreasing envelope 82 of FIG. 4 brings with it the advantage of reduced ultrasonic energy at harmonics of the fundamental frequency.

Once a waveform such as the waveform 80 of FIG. 4 has been designed, the waveform 80 can be coded into binary samples at a suitable sample rate and then stored in the waveform memory 44. The waveform memory 44 may be a read only memory, in which case the computer 64 may not be required to be connected to the transmit beamformer 40. Alternately, the waveform memory 44 may be a volatile memory which is programmed at power-up initialization by the computer 64. The computer 64 may perform any desired subset of the pulse designing steps described above. Typically, the desired pulse may be one of several selectable pulses included in a menu for user choice.

When the waveform in the waveform memory 44 is designed as described above, the result is a broad band waveform in the waveform memory 44 which simultaneously has substantially no radiated energy in a broad band centered on the harmonic. In the example of FIGS. 3 and 4, substantially no ultrasonic energy is radiated at frequencies above 4 MHz, or in a bandwidth of ±1 MHz with respect to the first harmonic (5 MHz). Preferably, the energy component at the harmonic is more than 30 dB reduced with respect to the magnitude of the fundamental frequency, and ideally is reduced by more than 40 dB.

Of course, it is not necessary to define the waveform 80 initially in the frequency domain. A Gaussian pulse can be defined in the time domain. Furthermore, the envelope need not be Gaussian, it may be some other window function such as a Hamming pulse, a modified Gaussian pulse, or any other suitable pulse. In some applications it may be preferable to use a narrow bandwidth pulse and thereby achieve a very high reduction of energy at the harmonic, since the harmonic of the lower bandedge is well above the upper bandedge. On other occasions it may be preferable to use a wider bandwidth pulse, for example, to obtain better axial (temporal) resolution. In this case, somewhat reduced reduction of energy at the harmonic may be accepted.

An alternative approach is to design the pulse 70 to ensure that substantially no energy is transmitted above 1.5 times the center frequency of the intended fundamental pulse (3.75 MHz in this case). It is preferable to limit low frequency energy in the transmitted pulse so that the harmonic energy associated with this frequency does not fall within the spectrum of the transmitted pulse. If the cut off frequency is 3.75 MHz, there should be very little transmitted energy below 1.875 MHz.

In designing the pulse 70 and the waveform 80, the Gaussian waveform may be passed through a high order, low pass filter to eliminate all harmonic energy. This filtering may be done off line in the computer 64.

Optimum imaging of the nonlinear contrast agent is obtained when the transmit beam insonifies the agent at power levels within a desired range. Power levels below this range may not be sufficiently high to cause the nonlinear contrast agent to radiate at the harmonic frequency. Power levels above this range may destroy the contrast agent prematurely. Additionally, since there are FDA limits on ultrasound intensity, a sharply focused transmit beam is not optimal. Such a sharply focused beam provides a high intensity (near the FDA limits) at the focus, but an intensity that is undesirably low at many other points along the associated receive scan line.

The receive beamformer 22 preferably receives samples along an entire scan line for each transmit event. For this reason, it is preferable that the region of insonification within the desired power level range be extended over a substantial portion of the length of the receive scan line. Thus, it is preferable that the intensity of the transmitted ultrasonic energy be substantially uniform and at a high level throughout the field of interest (which is typically a large fraction of the displayed depth).

The delay memory 42 preferably stores delay values to provide a controlled spread to the beam intensity in a way to optimize imaging of the contrast agent. Also, by making the intensity of harmonic energy received at the receive beamformer 22 more uniform throughout the field of interest, the levels of harmonic back scatter may be better controlled, resulting in manageable voltage swings at the receiver input.

Figure 5:
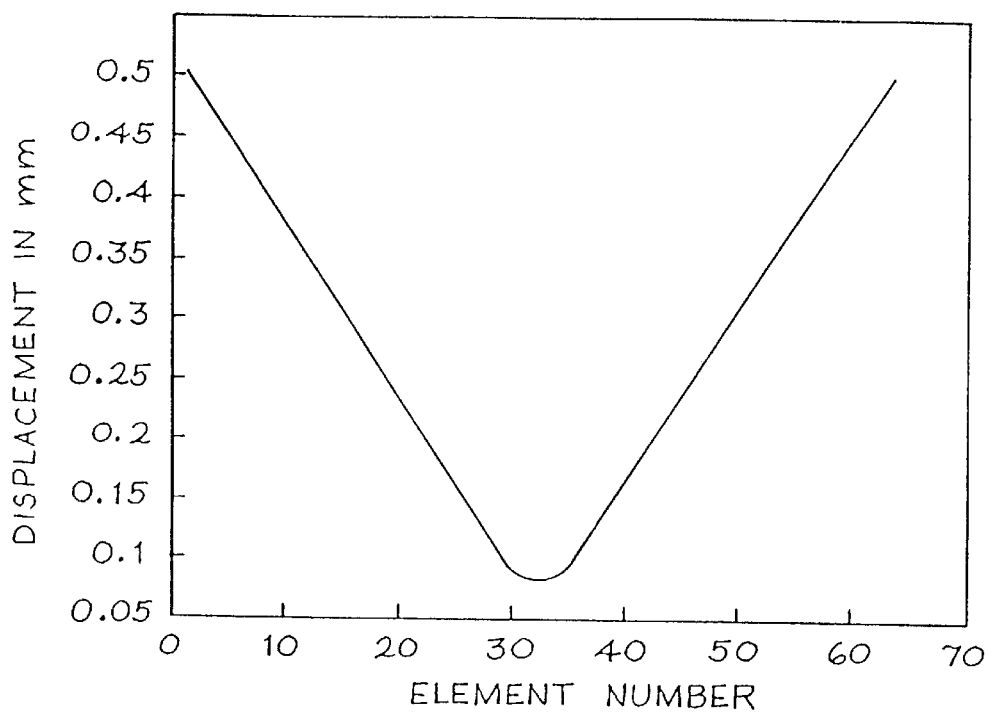
FIG. 5 is a graph of a focusing profile suitable for an axicon focus.

In this embodiment, the delay values stored in the delay memory 42 are selectively chosen to spread the beam along the current ultrasound line. One way to accomplish this is to use the well-known axicon focusing arrangement, as described, for example by C. Burckhardt in "Ultrasound Axicon: A Device for Focusing over a Large Depth" (J. Acoust. Soc. of Am., 54, 6, pp. 1628–1630 (1973)). The axicon focusing arrangement may utilize a focusing profile as shown in FIG. 5. Typically, this focusing profile provides a near focal limit corresponding to a circular arc centered on the near focal limit. Typically, the delay profile extends linearly outwardly from this circular arc to some outer limit, as shown in FIG. 5.

The objective is to spread the ultrasound energy throughout a region of the target, and many different delay profiles may accomplish this result. For example, the delay profile may be slightly curved, with a nonlinear variation of focal point with respect to transducer element position. There may be an outer focal limit, in which case the delay profile can include a circular portion at the ends of the array.

Figure 6:
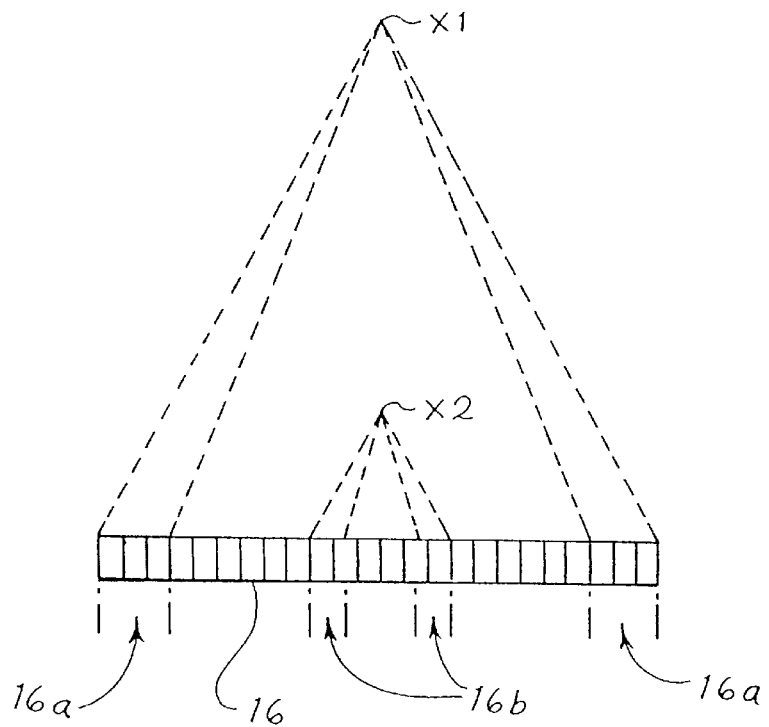
FIG. 6 is a schematic representation of a compound focus arrangement.

In many applications, it will be desirable to select the delay values in the delay memory 42 such that at least first frequency components of the transmit beam from at least a first plurality of transducers are focused at a first, shorter range, and that at least second frequency components of the transmit beam from at least a second plurality of transducers are focused at a second, longer range. One example is shown in FIG. 6, where substantially all of the ultrasonic energy from the transducers 16a at the end portions of the transducer array 16 are focused at a single longer range X1, and substantially all of the ultrasonic energy from the transducers 16b at central portions of the array are focused at a single, shorter range X2. By properly selecting the delay values, a line focus or a multiple-point compound focus may be obtained. When a line focus is used, the line may be straight or curved.

Another approach begins with focal delays required for a chosen focal point in the conventional manner. A random delay error is superimposed on these focal delays to smear or defocus the resulting beam. The greater the degree of defocusing, the more spread out the beam is. Preferably, a user control is provided to allow the user to vary the degree of defocusing by increasing the relative level of the defocusing delays. Also, it is preferable to increase the transmitted energy level to partially compensate for the loss of peak field intensity due to defocusing, either in an automatic (internally programmed) manner or under user control. The defocusing hardware can consist of a modified version of aberration correction hardware in which the delay corrections are pre-programmed random numbers rather than values which are continuously updated, for example by means of cross-correlating the waveforms from adjacent elements.

Conventional imaging at the fundamental frequency using an axicon or defocused beam is known to produce side lobes. However, such side lobes are not anticipated to create substantial problems in this application, particularly if the side lobes are below the harmonic activation threshold intensity and they therefore do not contribute to the generation of harmonic energy. Full dynamic receive focusing is preferably performed in the receive beamformer 22 to reduce the effect of side lobes in the transmit beam further.

Regardless of the precise configuration of the pulse 70 and the waveform 80, the waveform 80 preferably provides more uniform field intensity through a usefully extended depth of field. This results in more uniform generation of harmonic energy by the contrast agent and possibly a higher overall signal to noise ratio since more of the field is being unisonified at a sufficiently high power level to cause the contrast agent to radiate harmonic energy, but at a sufficiently low power level to prevent unnecessarily rapid destruction of the contrast agent.

If desired, the axicon focus may be obtained with a lens. Also, an axicon focusing scheme may be used in the elevation direction, if it is desired to increase the dimension of the insonified region in that direction.

Figure 7:
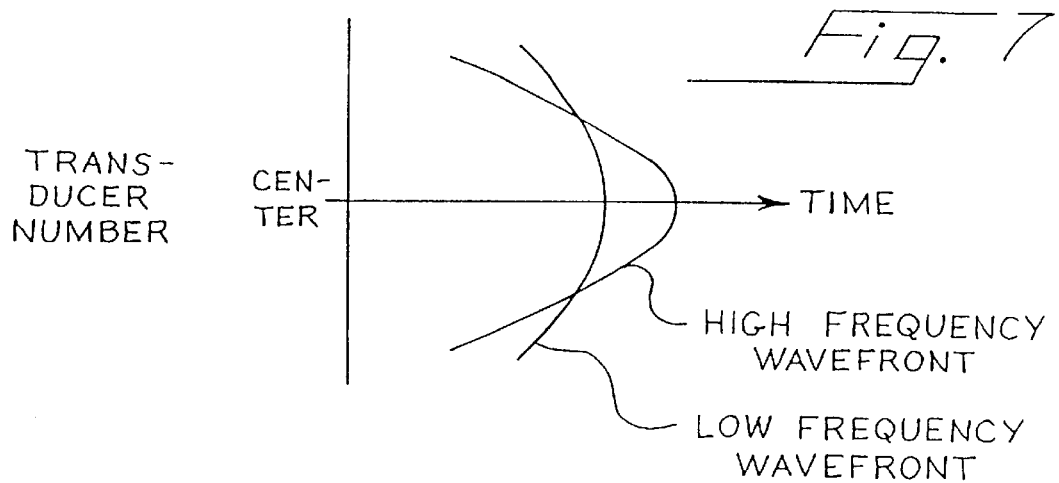
FIG. 7 is a graph showing high and low frequency wavefronts.
Figure 13:
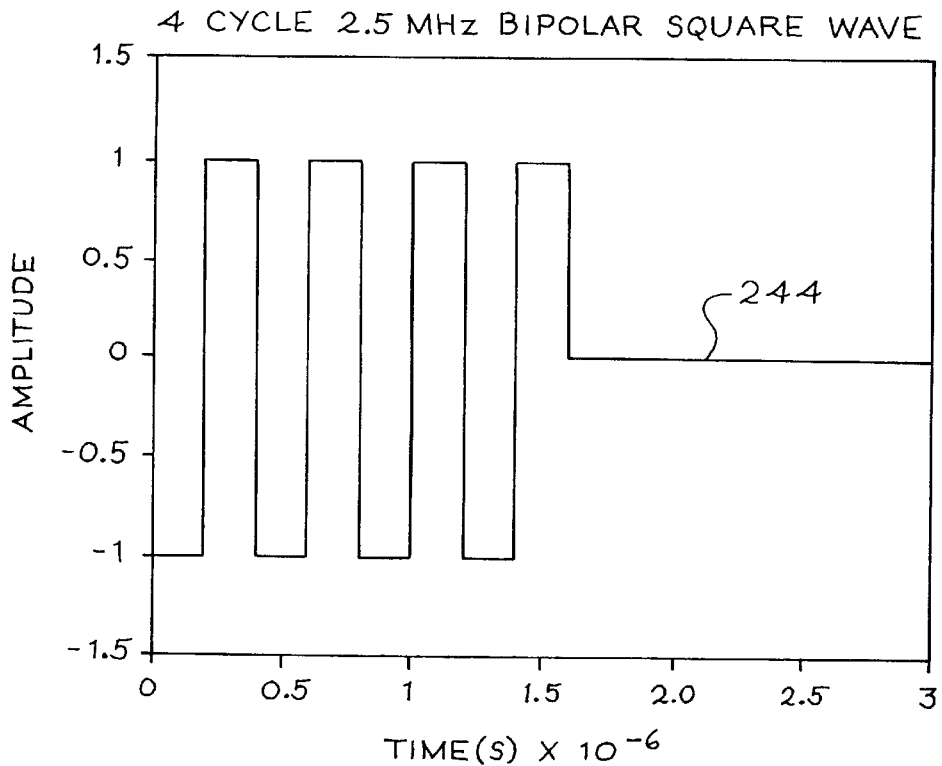

The transmit beamformer 40 of FIG. 2 is quite similar to the beamformer shown in FIG. 13 of U.S. Pat. No. 5,608,690, and the techniques described above relating to Gaussian waveforms modified to provide a line focus can be performed in the manner described in the above-identified application. Note in particular pages 23 and 24 of the above-identified application as filed, which expressly relate to optimized transmit beamformers for use with nonlinear contrast agents. With this approach, a plurality of transmit waveforms are provided, each for a respective one of the transducers of the transducer array. This plurality of transmit waveforms includes a central transmit waveform associated with a central one of the transducers. As explained in the above-identified patent application in detail, the central transmit waveform preferably comprises a lower frequency component and a higher frequency component, and a lower frequency component of the central transmit waveform occurs earlier in time than the higher frequency component of the central transmit waveform, as shown in FIG. 7. FIG. 7 corresponds to FIG. 11 of above-identified U.S. Pat. No. 5,608,690, and that application can be referenced for additional information regarding these figures. When the system of U.S. Pat. No. 5,608,690 is adapted for use with this invention, it is preferred that the frequencies along the line focus all be near the fundamental frequency to insonify the non-linear contrast agent effectively.

Additionally, the transmit beamformer described in Cole, et al., U.S. patent application Ser. No. 08/286,652, filed Aug. 5, 1994, and in U.S. patent application Ser. No. 08/432,056, filed May 2, 1995, both assigned to the assignee of the present invention, can be adapted for use with this invention. Once the desired output is defined as described above in terms of very low harmonic signal, one can then define the ideal output signal in the frequency domain and then convert it to the time domain. This time domain signal can then be divided by the carrier to obtain the desired envelope using complex shapes for both the time domain signal and the carrier. This combination of envelope and carrier can then be programmed into the transmit waveformer, using the parameters of attached Appendix 1. Appendix 1 provides parameters for both B-mode and Flow Mode. Appendix 3 provides a revised set of transmit beamformer parameters, and Appendix 4 provides a preferred set of transmit beamformer parameters adapted for use with the Acuson 3V2C transducer probe.

The envelope is sampled at a relatively low frequency, and as a result of imperfections in real implementations, remnants of harmonics relating to the sampling frequency of the carrier and the base band signal may appear in the final result.

In this example, harmonic energy at the second harmonic from the contrast agent is imaged using the receive beamformer described in Wright, et al. U.S. patent application Ser. No. 08/286,658, filed Aug. 5, 1994, and in U.S. patent application Ser. No. 08/432,615, filed May 2, 1995, both assigned to the assignee of the present invention. This receive beamformer can be programmed using the parameters of attached Appendix 2.

For example, the transmit beamformer of U.S. patent applications Ser. Nos. 08/286,652 and 08/432,056 can be operated with a nominal center frequency FO equal to 5.0 MHz, a transmit carrier frequency $F_c$ equal to 2.5 MHz, and a Gaussian envelope having a 50% bandwidth at −6.8 dB with ⅜ envelope sampling.

Figure 8:
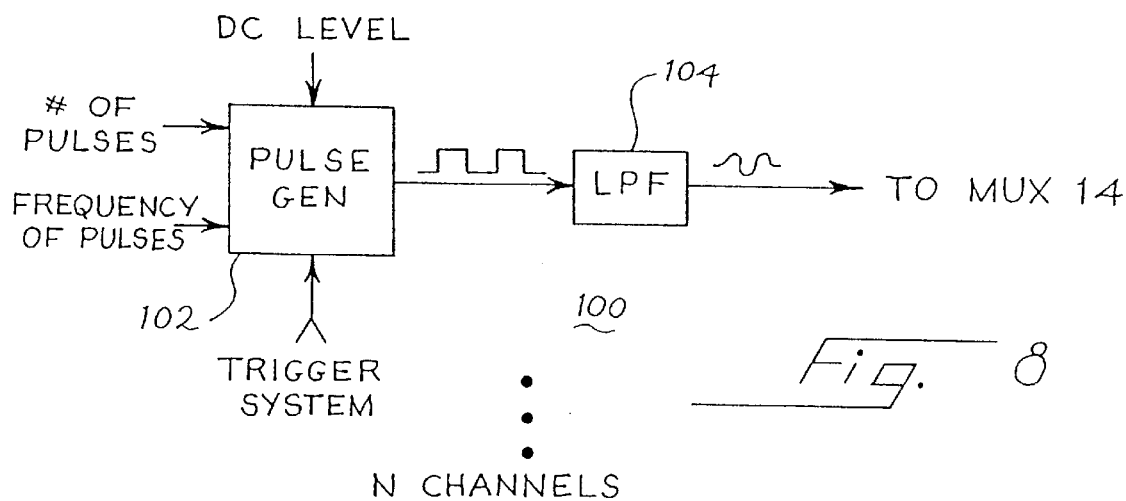
FIG. 8 is a block diagram of a second transmit beamformer suitable for use in the system of FIG. 1.

FIG. 8 shows another transmit beamformer 100 that can be used in the ultrasound imaging system 10. The beamformer 100 includes a pulse generator 102 which supplies a burst of pulses to a low pass filter 104. In this case, the pulse generator 102 switches between a selectable high voltage DC level and ground. The duration of the pulses and the number of pulses in the burst are controllable, as described, for example, in U.S. Pat. No. 4,550,067 (Maslak, et al.), assigned to the assignee of the present invention. The low pass filter 104 is designed as described above to substantially eliminate energy at the harmonic. The low pass filter 104 can be an analog filter such as a suitable Bessel or Chebyshev filter.

Figure 9:
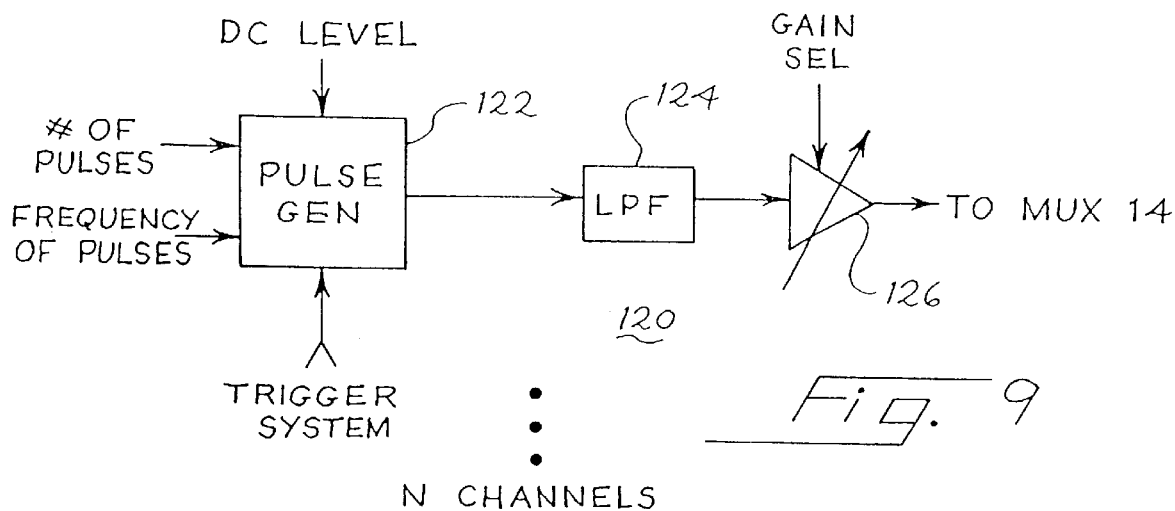
FIG. 9 is a block diagram of a third transmit beamformer suitable for use in the system of FIG. 1.

FIG. 9 shows another transmit beamformer 120 that can be used in the system 10 of FIG. 1. The transmit beamformer 120 includes a pulse generator 122 which supplies pulses to a low pass filter 124. The output of the low pass filter is supplied to a high voltage amplifier 126. Because the low pass filter 124 is applied prior to the amplifier 126, the low pass filter 124 can be designed with smaller components and hence can be higher order and more effective in suppressing harmonic energy.

It should be noted that conventional transducer arrays have a finite bandwidth, such as 75% at the −6 dB levels. Considering the example where the fundamental frequency is 2.5 MHz and the harmonic frequency is 5 MHz, the transducer will typically be centered between the transmit and receive frequencies (as for example at 3.75 MHz), with a relatively high bandwidth. Notice that when this transducer is operated at 2.5 MHz with a symmetrical band shape, the transducer will skew the transmitted spectrum toward higher frequencies. In the design of the transmitted pulse, the spectrum should preferably be modified to take account of the skewing effect of the finite bandwidth effects of the transducer and the fact that the transducer is working away from its center frequency in transmit.

Of course, the techniques described above can be used in systems 10 which provide apodization in the normal manner. If desired, apodization profiles can be modified if experience shows that the contributions from the end transducer elements (which are focused at deep ranges) are too attenuated. In this case, it may be preferable to increase the weighting at the end elements to compensate for this effect to some extent. By operating the end transducer elements at higher power levels than central transducer elements, more nearly uniform power levels are obtained at various ranges in the tissue being imaged.

A further modification is to use fewer transmit lines than receive lines. Since contrast agent tends to be consumed by the insonification process, it is preferable to reduce the number of transmit lines by reducing the frequency of firings and/or the spatial density of lines. Reduced firings and density can be achieved by firing one fourth the number of transmit lines and forming four synthetic receive lines closely spaced around each transmit line, which may be slightly defocused if required. Wright, et al. U.S. patent application Ser. No. 08/418,640, filed Apr. 7, 1995, assigned to the assignee of the present invention, discloses synthetic line systems that can be adapted for this purpose. Furthermore, frames of low intensity ultrasound may be interleaved with high intensity frames.

Multiple transmit zone firing (compound focus) may also yield a better result by spreading the beam between two selected focal regions. These techniques can be implemented on the transmit beamformer described in U.S. patent application Ser. No. 08/286,652, as described above.

It has been discovered that bipolar waveforms derived from switched DC levels can be filtered to provide effective suppression of ultrasonic energy at the harmonic. This can represent a substantial advantage, because bipolar, switched DC pulse sequences can be generated in a relatively inexpensive beamformer.

Figure 10:
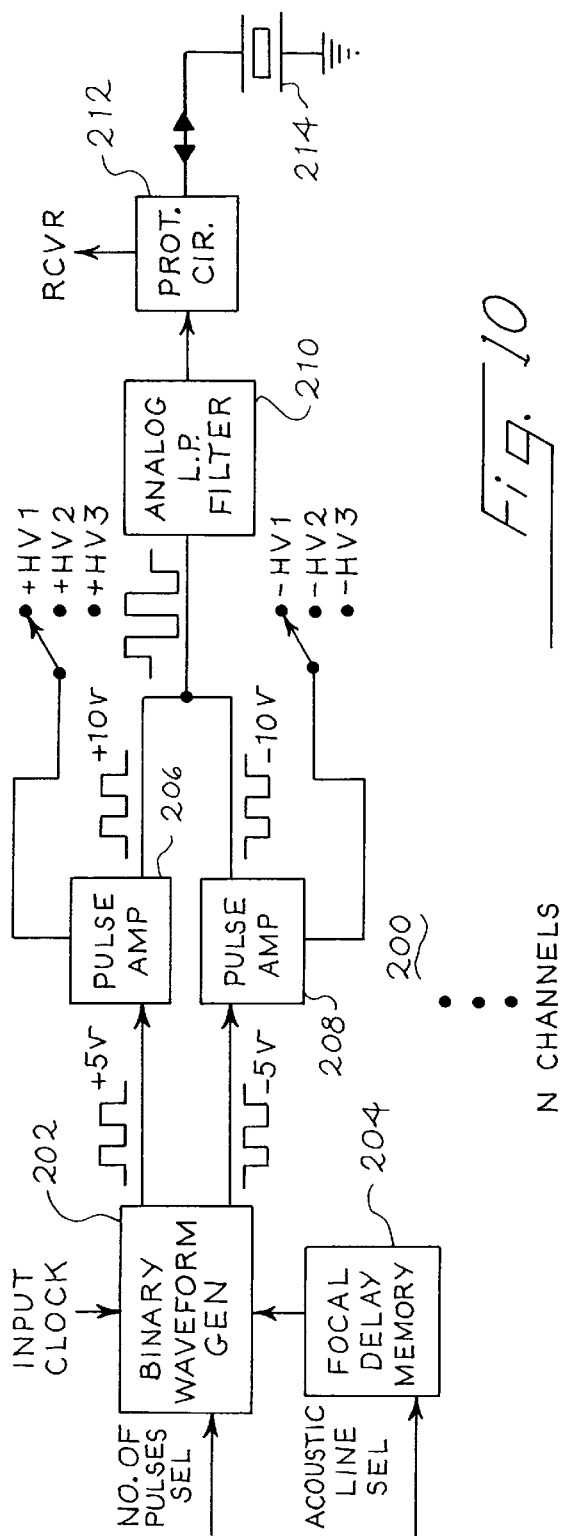

FIG. 10 shows a block diagram of one channel of a transmit beamformer 200 that utilizes such bipolar switched DC transmit waveforms. As shown in FIG. 10, each channel of the transmit beamformer 200 includes a binary waveform generator 202 that responds to inputs from an input clock, a select line defining the number of waveform cycles to be included in each pulse of energy, and a start input from a focal delay memory 204 that is in turn responsive to an acoustic line select input. Once the appropriate acoustic line has been selected, the focal delay memory 204 provides a start signal to the binary waveform generator 202 at the appropriate time, and the binary waveform generator 202 generates two output waveforms, which are 180° out of phase in this example.

These two waveforms are applied to respective pulse amplifiers 206, 208. Each of the pulse amplifiers 206, 208 responds to a high voltage input which can be switched to one of a plurality of levels such as 10, 20 and 50 volts in this example. The pulse amplifiers 206, 208 operate with positive and negative high voltage rails, respectively. Typically, each pulse amplifier 206 includes a transistor circuit used to switch the high voltage through the pulse amplifier 206, 208 to the output of the amplifier 206, 208. Each pulse amplifier outputs an amplified binary waveform, and the waveforms are summed at a summing node prior to being applied as an input to an analog lowpass filter 210. The signal applied as an input to the analog lowpass filter is a bipolar, switched DC transmit waveform. The output of the analog lowpass filter 210 is a filtered bipolar transmit waveform, which is applied to an ultrasonic transducer element 214 via a protection circuit 212. The protection circuit 212 is included to protect the receive electronics from high voltage transmit pulses. This circuit is typically based on a diode clamping circuit. Returning ultrasonic echoes from the target are converted by the transducer element 214 into electrical signals that are passed via the protection circuit 272 to a receiver (not shown), that typically includes a receive beamformer.

The analog lowpass filter 210 may be of any standard type. The filter 210 may comprise various resistors, inductors, and capacitors, and may include Bessel, Butterworth or Chebyshev filters, for example. Preferably, the filter 210 achieves approximately 20 dB of suppression at the second harmonic (two times the fundamental frequency). Ideally, the filter 210 may achieve a far higher degree of suppression. This may be achieved by using a high order filter, or a high suppression filter such as a Chebyshev filter. If desired, a multipole filter or a band pass filter can be used. In some applications, the components of the analog lowpass filter 210 are made switchable so that the cutoff frequency of the filter 210 can be varied according to the frequency characteristics of the transducer element 214 being used. This switching may be accomplished using relays or semiconductor analog switches such as those supplied by Supertex as HV2 type switches.

Although the filter 210 has been described above with respect to passive components, it should be understood that the filter 210 may be implemented using active filter circuits, including operational amplifiers for example. Such active filter circuits are well-known in the art, and are described for example in Horowitz and Hill, *The Art of Electronics*, Chapter 4 (Cambridge University Press, 1984).

Unipolar pulse sequences can also be formed using circuitry similar to that described in Maslak U.S. Pat. No. 4,140,022, which provides pulses having controllable amplitude, period, and pulse count. See also the description of pulse sequence transmitters in IEEE 1980 Ultrasonic Symposium, pp. 757–762 (Karrer, et al. "A Phased Array Acoustic Imaging System for Medical Use").

It is not required in all embodiments that the lowpass filter operate on the high voltage transmit waveform. An alternative beamformer 220 (FIG. 11) sums the two chopped DC output signals of a binary waveform generator 222 at a summer 223, and applies this summed signal as an input to a lowpass filter 224. The output of the lowpass filter 224 is applied to an adjustable gain amplifier 226 which amplifies the filtered signal to a voltage level appropriate for application to the transducer element 230 via the protection circuit 228. This approach allows the waveform to be generated and filtered at a relatively low voltage. This allows components rated at a lower voltage to be used in the filter 224, which may provide an important cost reduction.

As another alternative, the lowpass filter 210, 224 may include two components, one for each of the unipolar components of the transmit waveform prior to the point in the signal path where they are summed. See FIG. 11a, where the two components of the lowpass filter are shown at 232, 234

Figure 12:
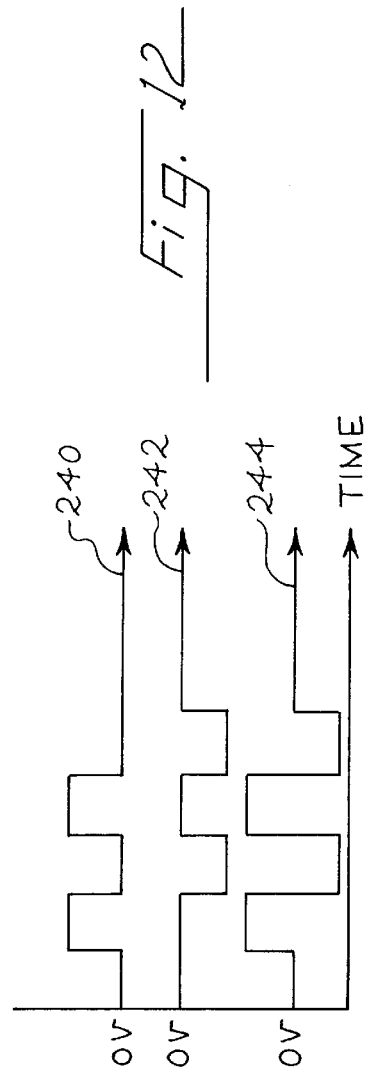

FIG. 12 provides waveforms that illustrate the operation of the transmit beamformers 200, 220. As shown in FIG. 12, the waveforms 240, 242 represent the output waveforms from the binary waveform generator 202, 222. Note that the positive excursions of the waveform 240 are out of phase by 180° with respect to the negative excursions of the waveform 242. The waveforms 240, 242 are best considered as unipolar components of the bipolar transmit waveform. The summation of the waveforms 240, 242 is shown at waveform 244. This summed waveform is bipolar in that it includes both positive and negative components, and is generated as described above as a sum of switched DC signals. The waveform 244 represents the bipolar transmit waveform that is applied as an input to the analog lowpass filters 210, 224.

Figure 14:
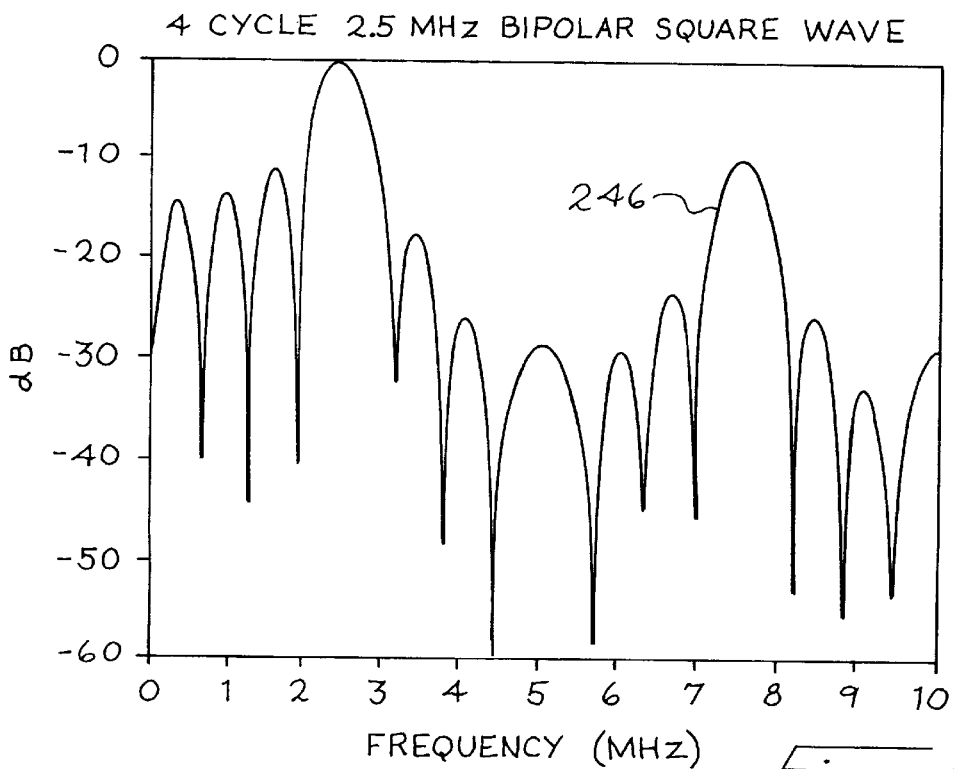

FIGS. 13 and 14 provide further information regarding the unfiltered bipolar transmit waveform 244. As shown in FIG. 13, this waveform displays excursions from +1 to −1 in an arbitrary amplitude scale, and it includes four cycles at a frequency of 2.5 MHz. FIG. 14 shows the frequency spectrum 246 of the bipolar transmit waveform 244 of FIG. 13. Note that maximum ultrasonic power is exhibited at the fundamental frequency (2.5 MHz), and that there is substantial power reduction (greater than −30 dB) at harmonics of the fundamental, such as 5 and 7.5 MHz.

Figure 15:
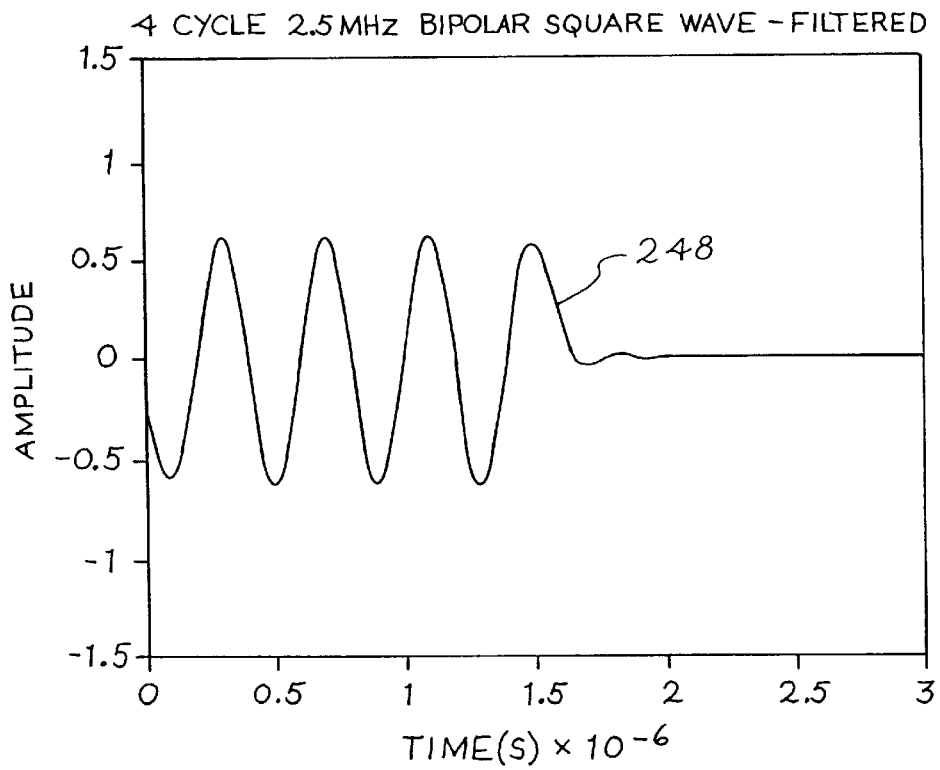
Figure 16:
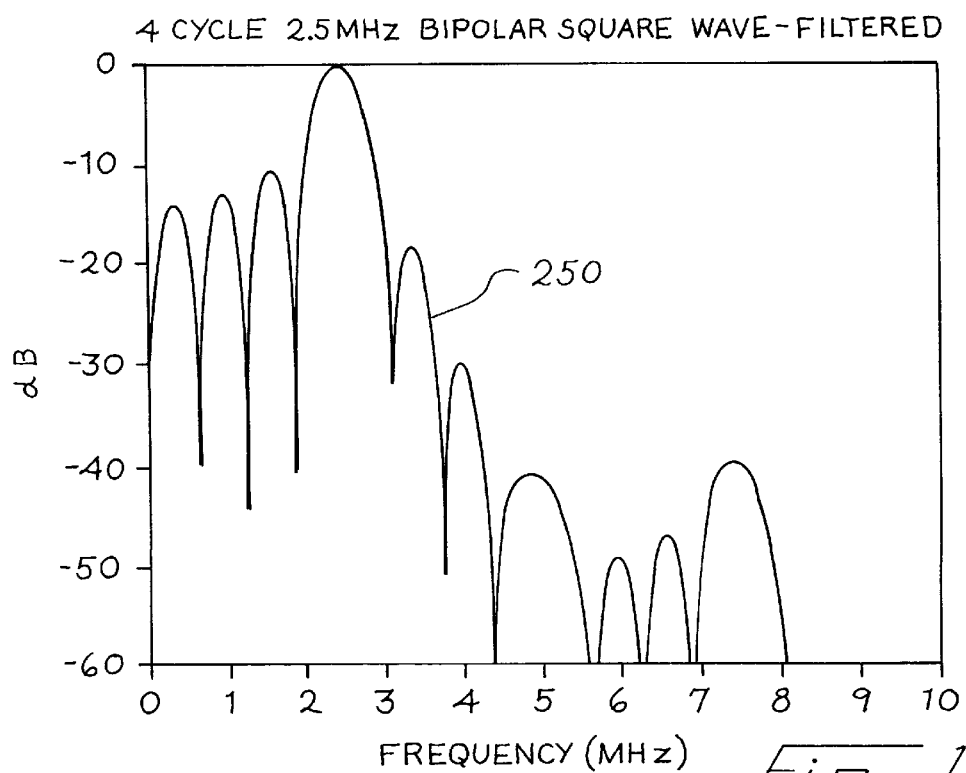

FIGS. 15 and 16 are corresponding graphs for the filtered bipolar transmit waveform supplied as an output of the analog lowpass filter 210, 224 of FIGS. 10 and 11 and the summer 223 of FIG. 11a. This filtered bipolar transmit waveform is identified as reference numeral 248, and includes four cycles with a fundamental frequency of 2.5 MHz. As shown in FIG. 16, the frequency spectrum 250 of the waveform 248 has substantially reduced power (by greater than 30 dB) at all frequencies greater than about 3.6 MHz.

Figure 17:
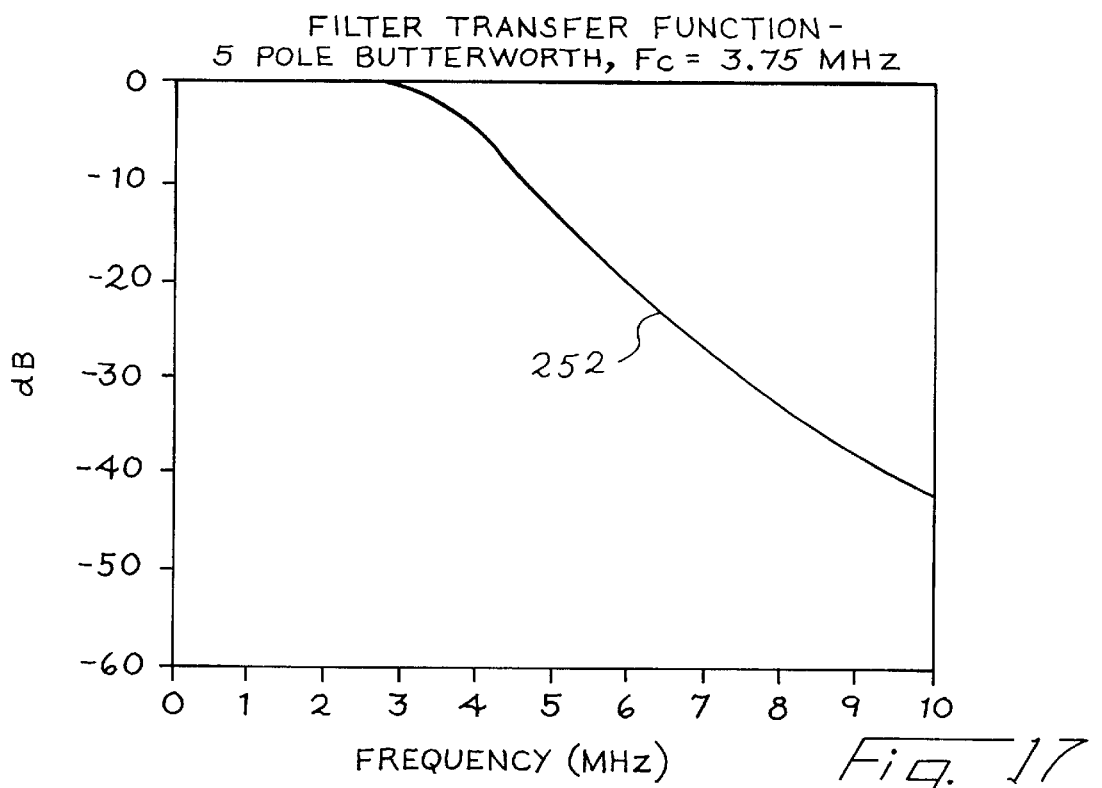

FIG. 17 provides a filter transfer function for a five pole Butterworth filter ($F_c$=3.75 MHz) that can be used for the lowpass filter 210, 224. This transfer function 252 reduces ultrasonic power at the harmonic 5 MHz with respect to the fundamental 2.5 MHz by more than 10 dB, and by about 13 dB in this example.

Of course, it will be understood by those skilled in the art that the voltage applied to the transducer elements in the beamformers 200, 220, 220' of FIGS. 10–11a described above will typically also be a function of transducer element number. Typically, apodization is employed so that end transducer elements are operated at a lower voltage than are the center transducer elements. This may be achieved by switching the high voltage input to the pulse amplifiers 206, 208 or by adjusting the gain select input for the amplifier 226 to different voltage levels according to the element position of the transducer element in the array. For example, the adjustable amplifier 226 can be a voltage controlled amplifier and the voltage control can be determined by apodization requirements.

FIGS. 18–23 relate to switched filter circuits that may be used in a method or a system for ultrasonic imaging in which ultrasonic energy is transmitted at a fundamental frequency to a target, and reflected ultrasonic energy at a harmonic of the fundamental frequency is received for imaging.

Figure 18:
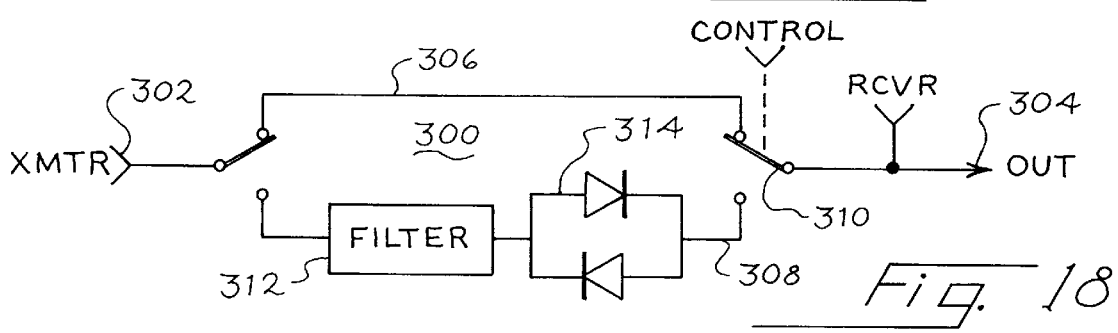
FIGS. 18–23 are block diagrams of alternative filter circuits suitable for use with ultrasonic harmonic imaging systems.

As shown in FIG. 18, the filter circuit 300 defines two signal paths. The first signal path proceeds from the input 302 via the conductor 306 to the output 304. The second signal path proceeds from the input 302 via the conductor 308 to the output 304. In this embodiment the second signal path includes a filter 312 and a isolation circuit 314.

The input 302 is intended to be coupled to the output of a ultrasonic transmitter, which can operate to generate unipolar, bipolar or shaped waveforms having substantial energy at the fundamental frequency. The output 304 of the filter circuit 300 is intended for connection either directly or indirectly to an ultrasonic transducer. For example, the output 304 may be coupled (either directly or indirectly) to a transducer connector or to a transducer cable. Similarly, the output 304 may be coupled to the input of an ultrasonic receiver as shown in FIG. 18, to a receiver protection circuit (not shown) or to a transmit/receive switch (not shown).

A switch 310 is controlled to select either the conductor 306 or the conductor 308. In a first mode of operation the switch 310 is positioned as shown in FIG. 18, and the transmitter is coupled to the transducer via the first signal path including the conductor 306. In this mode of operation the filter 312 is by-passed. In a second mode of operation the switch 310 can be placed by the control in connection with the conductor 308, and transmit signals from the transmitter to the transducer then pass through the filter 312 and the isolation circuit 314.

The filter 312 can be any suitable filter designed to suppress energy at the harmonic of interest. For example, the filter 312 can be a band reject filter centered about the second harmonic (or other desired harmonic such and third harmonic) of the fundamental frequency. Alternately, the filter 312 can be a bandpass filter centered on the fundamental frequency or a low pass filter.

The isolation circuit 314 is not required in all embodiments. However, it provides the advantage of avoiding electrical loading of the transducer elements or of the receiver input stage. Such loading is acceptable, but better performance may be obtained using the isolation circuit 314 in many cases.

Figure 19:
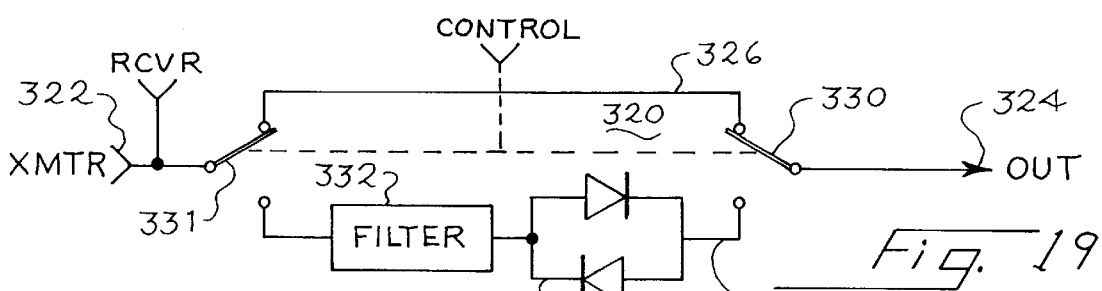

The filter circuit 320 of FIG. 19 is similar to that of FIG. 18, except two switches 330, 331 are provided, operated in parallel by the control. When the switches 330, 331 are positioned as shown in FIG. 19, the input 322 is connected via the conductor 326 to the output 324, and both the filter 332 and the isolation circuit 334 are completely isolated from the signal path. When the switches 330, 331 are in the opposite position, in which the selected signal path includes the conductor 328, signals passing from the transmitter to the transducer are passed through the filter 332 on the isolation circuit 334.

In FIG. 19 the receiver input is connected adjacent the input 332, and the switches 330, 331 can automatically be controlled such that they are placed in the state shown in FIG. 19 during receive operations and are automatically switched to the opposite state for transmit operations.

Figure 20:
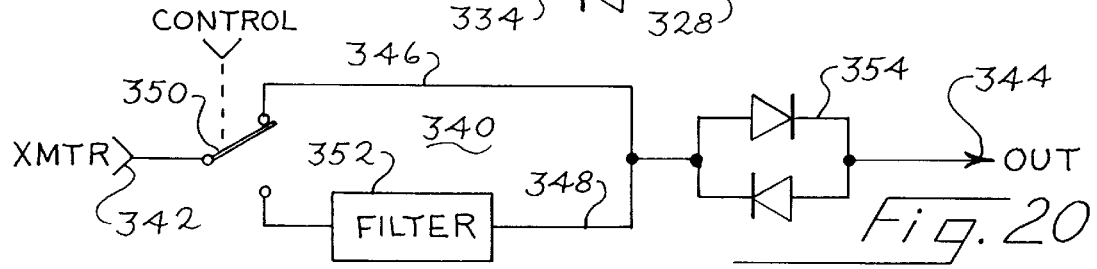

The filter circuit 340 of FIG. 20 is similar to the circuit 300 of FIG. 18, with two exceptions. In this case the switch 350 has been placed adjacent the input 342, and the isolation circuit 354 has been moved adjacent the output 344. Thus, signals pass through the isolation circuit 354 regardless of whether the switch 350 routes transmit pulses via the conductor 346 or via the filter 352 and the conductor 348.

Figure 21:
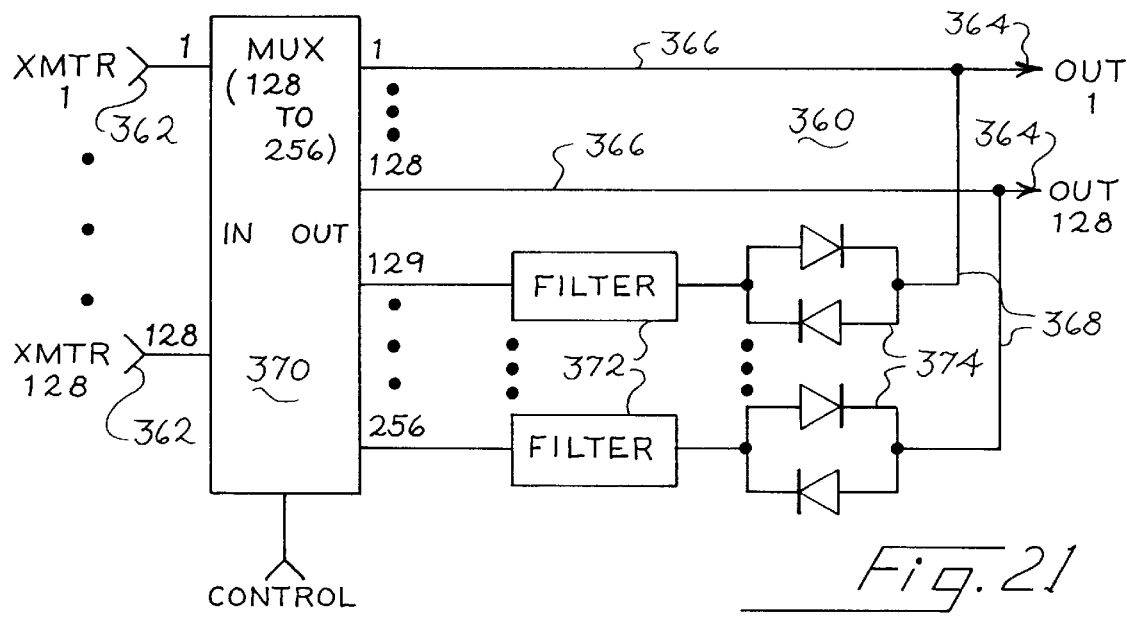

As shown in FIG. 21, a filter circuit 360 can be provided which provides two signal paths including conductors 366 and 368, respectively, between an input 362 and an output 364 for each of 128 channels. The following discussion refers only to channel 1, but the other channels are configured similarly. In this case the filter circuit 360 includes a 128 channel 1:2 multiplexer 370 that switches the transmitter signal applied to the input 362 either to output terminal 1 (connected to conductor 366) or to output terminal 129 (connected to filter 372, isolation circuit 374 and conductor 368). Thus, in a first mode of operation of the multiplexer 370, transmitter output signals on each of 128 channels are routed via the respective inputs 362 and the respective conductors 366 to the respective outputs 364, thereby bypassing the filters 372 and the isolation circuits 374. In a second mode of operation as selected by the control, transmit signals are routed from the inputs 362 via the respective filters 372, isolation circuits 374, and conductors 368 to the respective outputs 364, thereby placing the filters 372 and the isolation circuits 374 in the signal paths.

In any of the embodiments of FIGS. 18–21 the isolation circuits can be eliminated, they can be placed as shown in FIG. 20 in a common portion of the first and second signal paths, or they may be placed as shown in FIGS. 18, 19 and 21 in only one of the signal paths. Also as shown in FIGS. 18–21 the receiver can if desired be connected to the combined signal paths either upstream or downstream of the filter. In the event the receiver is connected upstream of the filter as shown in FIG. 19, the switch or switches should be controlled to prevent the filter from operating in the receive mode, at least in those cases where the receiver is responsive to harmonic ultrasonic energy. In cases such as FIG. 18 where the receiver is connected to the signal path downstream of the filter, the switch 310 can be controlled to bypass the filter 312 selectively, as for example when the transmitter is used in an alternative mode of operation in which both the transmitter and the receiver are centered at the same fundamental frequency.

As shown in FIG. 21, the switches for the filters may be part of a pre-existing transducer multiplexer.

Figure 22:
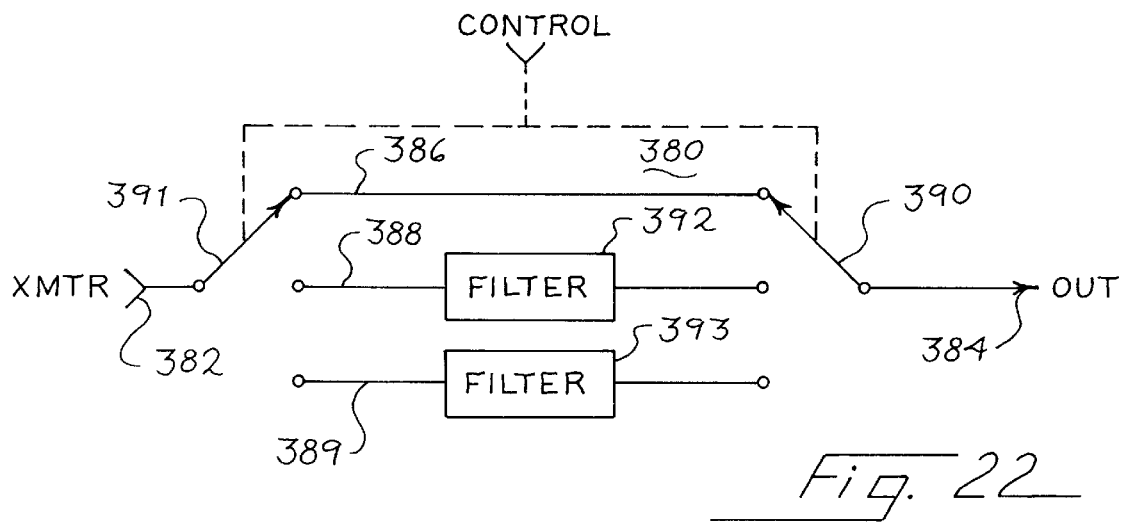

FIG. 22 is a schematic diagram of a filter circuit 380 that is similar to the filter circuit 320 of FIG. 19 with two exceptions. First, the filter circuit 380 does not include an isolation circuit. As explained above, such isolation circuits are optional. Second, the filter circuit 380 includes a total of three signal paths 386, 388, 389 between the input 382 and the output 384. The switches 390, 391 route signals from the transmitter to the output via anyone of these three signal paths. The signal path 386 includes no filter while the signal paths 388, 389 include separate respective filters 392, 393. The filters 392, 393 may for example be band pass filters appropriate for two different fundamental frequencies. In some applications, the unfiltered signal path 386 can be eliminated.

Figure 23:
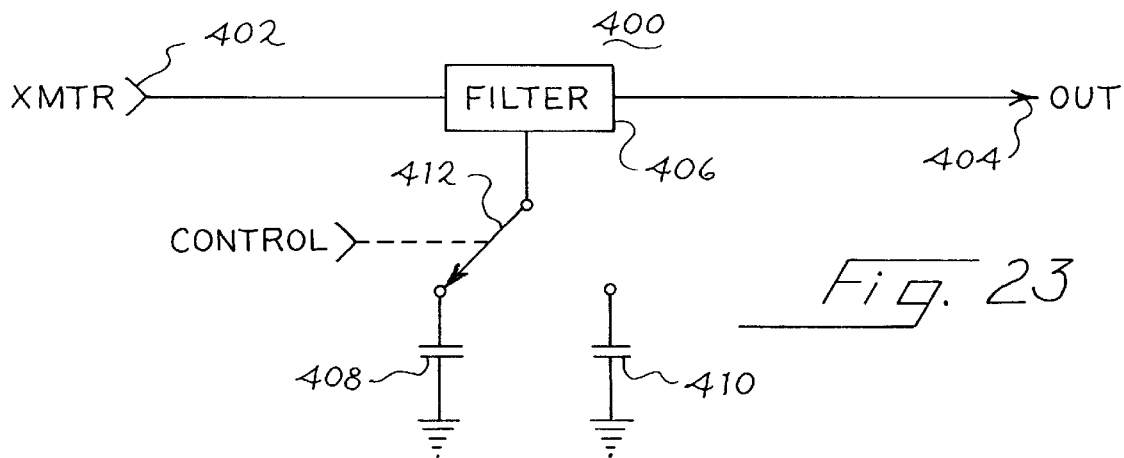

The filter circuit 400 of FIG. 23 includes a filter circuit 406 interposed between an input 402 and an output 404. In this case the filter circuit 406 includes component filters 408, 410, and a switch 412 is used to connect the signal path containing the desired one of the component filters 408, 410 to the filter circuit 406. In this way, the filter characteristics of the filter circuit 406 can be adjusted as appropriate for the particular application by controlling the switch 412 to select the appropriate one of the filters 408, 406. As used herein, the term "filter" is intended broadly to encompass both filter circuits such as low pass, band pass, or band blocking filter circuits as well filter components such as capacitors, inductors and other electrical components that affect the filter characteristics of a filter circuit.

Switched filters similar to any of those shown in FIGS. 18–23 may be used in the systems shown in FIGS. 2, 8, 9, 10, 11 and 11a. For example, switched filters (using any of the approaches described above) may be substituted for the unswitched filter 58 of FIG. 2, the filter 104 of FIG. 8, the filter 124 of FIG. 9, the filter 210 of FIG. 10, the filter 224 of FIG. 11, or the filters 232, 234 of FIG. 11a.

In the systems described above, bi-polar rectangular or uni-polar transmit waveforms may also be shaped. The amplitude of each transmit waveform is shaped to gradually rise to a maximum value and gradually decrease from the maximum value. Each transmit waveform is shaped by modulating a carrier waveform with an envelope waveform. Alternatively and with respect to transmitting a uni-polar waveform, a shaped low pass off-set waveform with a gradually increasing and decreasing amplitude is summed with a bi-polar waveform in real-time or off-line. Shaping the amplitude of bi-polar rectangular or uni-polar transmit waveforms to reduce energies associated with harmonic frequencies is discussed in U.S. application Ser. No. 08/893, 150 for Ultrasonic Imaging Method And System For Transmit Signal Generation For An Ultrasonic Imaging System Capable Of Harmonic Imaging, assigned to the assignee of the present invention and filed on Jul. 15, 1997, the disclosure of which is hereby incorporated by reference.

As yet another alternative embodiment, the transmit waveforms discussed above may be pulse width modulated. As disclosed in U.S. Ser. application No. 08/893,287 now U.S. Pat. No. 5,833,614, for Ultrasonic Imaging Method and Apparatus For Generating Pulse Width Modulated Waveforms With Reduced Harmonic Response, assigned to the assignee of the present invention and filed on Jul. 17, 1997, the disclosure of which is hereby incorporated by reference, the duration of each pulse within a burst is selected to reduce the energy transmitted at harmonic frequencies. In particular, the duration of one or more pulses is different than other pulses within the burst. Preferably, the widths of the pulses within the burst gradually increase and then decrease, but other duration patterns may be used.

As yet another alternative embodiment, the transmit waveforms discussed above may be shaped as a function of summation of the waveforms in the acoustic domain. As disclosed in U.S. application Ser. No. 08/893,271, now abandoned, for Ultrasonic Imaging Method And System For Harmonic Imaging Pulse Shaping In The Acoustic Domain, assigned to the assignee of the present invention and filed on Jul. 15, 1997, the disclosure of which is hereby incorporated by reference, the transmit waveform associated with a first transducer element or elements is shaped relative to a second waveform associated with a second transducer element or elements. For example, the first waveform (1) is delayed by a fraction of a cycle or one or more cycles, (2) is adjusted in amplitude, (3) is transmitted for a different number of cycles or (4) any combination of two or all three of (1), (2), and (3) relative to the second waveform. The first and second waveforms are focused at a point and transmitted. The transmitted waveforms sum in the acoustic domain at the point to form the desired waveform for reduction of energies transmitted in the harmonic frequencies. Preferably, the desired waveform corresponds to an amplitude that rises gradually to a maximum value and decreases gradually from the maximum value.

As an example of generating transmitted waveforms as a function of the resulting summed signal in the acoustic domain, the first and second waveforms are rectangular waves. The first waveform is delayed, in addition to any focusing delay, by may be ¼ of a cycle relative to the second waveform. At the point in the body, the first and second waveform sum together to form a third waveform. The third waveform has three amplitude levels (0,1,2). The greatest amplitude is associated with an overlap of the first and second transmit waveforms and is preferably at the center of the third waveform. The number of cycles and amplitude shape of the first and second waveforms may also be controlled to create the desired third waveform in the acoustic domain.

Any of the various alternatives discussed above, such as pulse width modulation, filtering, generation of waveforms with multiple amplitudes and summation of waveforms in the acoustic domain, may be used in combination. The combination may include more than two of the alternatives discussed above.

All of the harmonic imaging techniques described above can be used in both tissue and contrast agent harmonic imaging modes. In the tissue harmonic imaging mode no additional non-linear contrast agent is added to the target, and only the native non-linear characteristics of the tissue are relied on to create the ultrasonic image. Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. In this case no additional non-linear contrast agent is introduced into the tissue at any time during the imaging session. In the contrast agent harmonic imaging mode, any one of a number of well known non-linear contrast agents such as those described above can be added to the target in order to enhance the non-linear harmonic response of the tissue. For this reason, it should be understood that the introduction of an added non-linear contrast agent into the tissue being imaged is not implied in any of the following claims unless such added non-linear contrast agent is expressly recited.

From the foregoing, it should be apparent that improved systems and methods for imaging contrast agent have been disclosed. These systems can use the transmit beamformers described in U.S. Pat. No. 5,608,690, which focuses different frequency components at different ranges. Also, as described above, these techniques can be used with other beamformers which utilize other transmit waveforms. Of course, the various aspects of this invention relating to harmonic suppression and line focus (or other spreading of the region of maximum intensity) can be used separately from one another, rather than in combination as described above. It is intended that the foregoing detailed description be regarded as illustrative rather than limiting. It is the following claims, including all equivalents, which are intended to define the scope of this invention.

APPENDIX 1

Parameters for Transmit Beamformer (all references are to FIG. 3 of U.S. patent application Ser. No. 08/432,056)

| Parameter | Corresponds to | Value |
|---|---|---|
| h2 | FIR filter h2 of T312 | [1 4 6 4 1] |
| h3 | FIR filter h3 of T324 | [1 0 −2 0 1] |
| Ku2 | Upsampler of T326 | 2 |
| Ku1 | Upsampler of T312 | 2 (determined by: Ku1=Nb*4/Ku2) |
| h4 | FIR filter h4 of T326 | [2 3 2] |
| Nb | Number of transmit beams | 1 |
| cw_on | | 0 −> pulsed mode |
| Envelope Type, beam 0 | 'Env len' of FIG. 4 | 0 −> real |
| Ns | | B-mode: 17 |
| | | F-mode: 23 |
| h1 | Envelope in T304 | B-mode: [0.0039, 0.0156, 0.0430, 0.1133, 0.2461, 0.4531, 0.7031, 0.9141, 0.9961, 0.9141, 0.7031, 0.4531, 0.2461, 0.1133, 0.0430, 0.0156, 0.0039] (33% Gaussian, sampled at Fe=10Ms/s) |
| | | F-mode: [0.0039, 0.0078, 0.0195, 0.0430, 0.0898, 0.1719, 0.2930, 0.4531, 0.6406, 0.8203, 0.9492, 0.9961, 0.9492, 0.8203, 0.6406 0.4531, 0.2930, 0.1719, 0.0898, 0.0430 0.0195, 0.0078, 0.0039] (25% Gaussian, sampled at Fe=10MS/s) |
| phi | Phase to be applied at T310 | See definition of phi below |
| Fs | Sampling Freq at O/P of T328 | 40MS/s |
| Fe | Sampling Freq of envelope in T304 | 10MS/s (determined from above based on: Fe=Fs/Ku1/Ku2) |
| Fpa select | v_phi=Fc/F0 | 0 −> use modulation frequency for focusing |
| Fm/F0 | v=Fc/F0 | 0.5 (Fm=2.5 MHz; F0=5.0 MHz) |
| F0 | | 5.0 MHz |

Together these terms, plus the fact that the envelope is real, are used to calculate the phase applied in complex multiplier T310, as described in application Ser. No. 08/432,056. In particular, this phase if broken into:

envelope phase -- zero because envelope is real
    fine focusing -- calculated from the difference between quantized and ideal delay, using the phase alignment frequency vphi=v
    modulation -- complex multiplier T310 includes a component which corresponds to modulation to a frequency (Fm/F0−1)*F0. This modulation, in combination with later modulation in complex multiplier T318, results in an overall effective modulation frequency Fm.

phi = phi_D + phi_E + phi_R
    phi_D (Phase portion of delay (fine focusing)) = −2.(pi).v_phi.tau_phi
        tau_phi = low order portion of the delay word representing fractional units of T0 (1/F0) as in Pat. application 08/432,056.
        This is the portion of the specified focusing delay which is applied via phasing rather than true time delay
    phi_E = 0 (Waveform sample phase is zero because envelope is real)
    phi_R = 2.(pi).ku1.(v − 1).n/4 (n is the successive sample number)
        This is a phase rotation of 2.(pi).(Fm − F0).t where t =ku1.t / (4.F0)

APPENDIX 2

Parameters for Receive Beamformer (all references are to FIG. 3 of U.S. patent application Ser. No. 08/432,615)

| Parameter | Corresponds to | Value |
|---|---|---|
| Fs | Sampling rate Fs at ADC | 40 MS/s |
| Nb | Number of receive beams | 2 |
| Kd1 | Downsampler of R162 | 2 |
| h1 | FIR filter h1 of R160 | [2 3 2] (selected based on Kd1) |
| h1 bypass | | disabled |
| h2 | FIR filter h2 of R164 | [1 0 −1] |
| h2 bypass | | disabled |
| h3 | FIR filter h3 of R167 | [1 4j −8 −10j 8 4j −1] |
| h3 bypass | | disabled |
| Kd2 | Downsampler of R169 | 4 (determined by: Kd2=Nb*4/Kd1) |

APPENDIX 2-continued

Parameters for Receive Beamformer (all references are to FIG. 3 of U.S. patent application Ser. No. 08/432,615)

| Parameter | Corresponds to | Value |
|---|---|---|
| | | 5 MS/s (determined from above, based on Fb=Fs/Kd1/Kd2) |
| Fp select | | 0 -> Fp = Fstart |
| Fd select | | 1 -> Fd = Fstart - Fdownslope*R |
| Fstart/F0 | Fstart | B-mode: Fstart/F0=1.1172 (5.5859 MHz) |
| | | F-mode: Fstart/F0=1.0781 (5.3906 MHz) |
| Fdownslope | {DELTA F sub downshift} | B-mode: Fdownslope = 1.793E-4 F0/T0 <--> 5821 Hz/mm |
| | | F-mode: Fdownslope = 1.144E-4 F0/T0 <--> 3716 Hz/mm |
| Tbreak | | Tbreak >= 1792 T0 (276 mm) |
| Fupslope | | 0 |
| Base Band Filter | | |
| = = = | | |
| Ntaps | | 16 |
| type | | real |
| L/M ratio | | 1/1 (based on L=1, M=1) |
| hbbf | Base band filter coefficients | (based on L=1, M-1) |
| | | B-mode: hbbf= [0, 0, 0, 0, 0, 0.0195, 0.0996, 0.2285, 0.2988, 0.2285, 0.0996, 0.0195, 0, 0, 0, 0] |
| | | F-mode: hbbf= [0, 0, 0, 0.0020, 0.0137, 0.0469, 0.1172, 0.1992, 0.2383, 0.1992, 0.1172, 0.0469, 0.0137, 0.0020, 0, 0] |
| | | Baseband filter is an FIR operating on the output of the receive beamformer |

APPENDIX 3

Revised Parameters for Transmit Beamformer

All parameters are as defined in Appendix 1 and are set equal to the values of Appendix 1 except as noted.

H3=[1 0 -1]
Ns=17 (B-mode)
   17 (F-mode)
B-mode Envelope = [.01171875  .03125     .078125    .16796875  .3203125
                   .52734375  .75        .9296875   .99609375  .9296875
                   .75        .52734375  .3203125   .16796875  .078125
                   .03125     .01171875]
(29% Gaussian, sampled at Fe=10MS/s)
F-mode Envelope = [.01562     .0390625   .08984375  .19140625  .34375
                   .546875    .765625    .93359375  .99609375  .93359375
                   .765625    .546875    .34375     .19140625  .08984375
                   .0390625   .015625]
(30% Gaussian, sampled at Fe=10MS/s)

APPENDIX 4

Second Revised Parameters for Transmit Beamformer (Adapted for use with Acuson 3V2C Probe)

All parameters are as defined in Appendix 1 and are set equal to the values of Appendix 1 except as noted.

H3=[1 0 -1]
Ku2=4
Ku1=1
Ns=27
Envelope= [0.015625   0.03125     0.0546875   0.08984375
           0.140625   0.21484375  0.30859375  0.41796875
           0.546875   0.6796875   0.80078125  0.90625
           0.97265625 0.99609375  0.97265625  0.90625
           0.80078125 0.6796875   0.546875    0.41796875
           0.30859375 0.21484375  0.140625    0.08984375
           0.0546875  0.03125     0.01562500]
(33% Gaussian, sampled at Fe=14MS/s)
Fs=56MS/s
Fe=14MS/s
F0=3.5 MHz

We claim:

1. A method for ultrasonically imaging a target during an imaging session, said method comprising the following steps:

(a) transmitting ultrasonic energy in power bursts at a fundamental frequency into the target, said target being free of added nonlinear contrast agent throughout the entire imaging session, each power burst comprising a respective envelope shape, each envelope shape rising gradually to a respective maximum value and falling gradually from the respective maximum value; and (b) receiving reflected ultrasonic energy from the target at a harmonic of the fundamental frequency.

2. The method of claim 1 wherein said power bursts are characterized by a power level at the harmonic which is reduced by at least 30 dB with respect to ultrasonic power in the power burst at the fundamental frequency.

3. The method of claim 1 wherein said power bursts are characterized by a power level at the harmonic which is reduced by at least 40 dB with respect to ultrasonic power in the power burst at the fundamental frequency.

4. A method for ultrasonically imaging a target during an imaging session, said method comprising the following steps:

(a) generating a transmit waveform;

(b) filtering the transmit waveform with a filter adapted to reduce ultrasonic energy in the transmit waveform at a harmonic of a fundamental frequency by at least 30 dB with respect to the fundamental frequency;

(c) transmitting the filtered transmit waveform into the target, said target being free of added nonlinear contrast agent throughout the entire imaging session; and (d) receiving reflected ultrasonic energy from the target at the harmonic of the fundamental frequency.

5. The method of claim 4 wherein the filter is adapted to reduce ultrasonic energy in the transmit waveform at the harmonic of the fundamental frequency by at least 40 dB with respect to the fundamental frequency.

6. A method for ultrasonically imaging a target during an imaging session, said method comprising the following steps:

(a) generating a transmit waveform with a programable waveform generator such that ultrasonic power in the transmit waveform at a harmonic of a fundamental frequency is reduced by at least −30 dB with respect to ultrasonic power in the transmit waveform at the fundamental frequency;

(b) transmitting the transmit waveform into the target, said target being free of added non-linear contrast agent throughout the entire imaging session; and (c) receiving reflected ultrasonic energy from the target at the harmonic of the fundamental frequency.

7. The method of claim 6 wherein ultrasonic power in the transmit waveform at the harmonic of the fundamental frequency is reduced by at least 40 dB with respect to ultrasonic power in the transit waveform at the fundamental frequency.

8. A method for ultrasonically imaging a target during an imaging session, said method comprising the following steps:

(a) transmitting ultrasonic energy at a fundamental frequency into the target in a transmit beam having a line focus, said target being free of added non-linear contrast agent throughout the entire imaging session; and (b) receiving reflected ultrasonic energy from the target at a harmonic of the fundamental frequency.

9. The method of claim 8 wherein the step (a) comprises the step of phasing a plurality of transmit waveforms to form the line focus for the transmit beam.

10. A method for ultrasonically imaging a target during an imaging session, said method comprising the following steps:

(a) transmitting ultrasonic energy at a fundamental frequency into the target in a transmit beam having an elongated high power region by focusing at least first selected frequency components from at least selected transducer elements at a first range and focusing at least second frequency components from at least selected transducer elements at a second range, said target being free of added nonlinear contrast agent throughout the entire imaging session; and (b) receiving ultrasonic energy from the target at a harmonic of the fundamental frequency.

11. The method of claim 10 wherein step (a) comprises the step of phasing a plurality of transmit waveforms to form the transmit beam having the elongated high power region.

12. The method of claim 11 wherein the plurality of transmit waveforms comprises a central transmit waveform associated with a central one of the transducers, wherein the central transmit waveform comprises a lower frequency component and a higher frequency component, and wherein the lower frequency component of the central transmit waveform occurs earlier in time than the higher frequency component of the central transmit waveform.

13. The method of claim 10 wherein the first range is greater than the second range, and wherein the first selected frequency components are characterized by a higher power level than the second selected frequency components.

14. The method of claim 10 wherein step (a) comprises the step of varying apodization of the transducer elements to achieve more nearly uniform ultrasonic energy levels at the first and second ranges.

15. A method for ultrasonically imaging a target during an imaging session, said method comprising the following steps:

(a) transmitting ultrasonic energy in power bursts at a fundamental frequency into a target, said target being free of added non-linear contrast agent throughout the entire imaging session, each power burst characterized by a respective frequency spectrum having a respective center frequency, a respective peak amplitude, and a respective bandwidth, the bandwidth of each power burst being at least about 30% of the respective center frequency at points −6.8 dB with respect to the respective peak amplitude, said frequency spectra reduced at a harmonic by more than 30 dB with respect to the peak amplitude.

(b) receiving ultrasonic energy from the target at the harmonic of the fundamental frequency.

16. The method of claim 15 wherein the bandwidth of each power burst is at least about 50% of the respective center frequency at points −6.8 dB with respect to the respective peak amplitude.

17. The method of claim 15 or 16 wherein the frequency spectra are reduced at the harmonic by at least about 50 dB with respect to the peak amplitude.

18. In a method for imaging a target during an imaging session, said method comprising the steps of (a) transmitting ultrasonic energy at a fundamental frequency, and (b) receiving reflected ultrasonic energy at a harmonic of the fundamental frequency, the improvement wherein step (a) comprises the step of:

(a1) transmitting ultrasonic energy in power bursts into a target which is free of added non-linear contrast agent throughout the entire imaging session, each power burst characterized by a respective frequency spectrum having a respective peak amplitude near the fundamental frequency, said frequency spectrum reduced within a first bandwidth greater than or equal to ±X% of the harmonic of the fundamental frequency by more than Y dB with respect to the peak amplitude, where X is equal to 5 and Y is equal to 30.

19. The method of claim 18 wherein X is equal to 10.

20. The method of claim 18 wherein X is equal to 15.

21. The method of claim 18 wherein X is equal to 20.

22. The method of claim 18 wherein X is equal to 10 and Y is equal to 50.

23. The method of claim 18 wherein X is equal to 15 and Y is equal to 50.

24. The method of claim 18 wherein X is equal to 20 and Y is equal to 50.

25. The method of claim 18 or 19 or 20 or 21 or 22 or 23 or 24 wherein each frequency spectrum has a respective center frequency, a respective peak amplitude, and a respective second bandwidth, the second bandwidth of each frequency spectrum being at least about 30% of the respective center frequency at points −6.8 dB with respect to the respective peak amplitude.

26. The method of claim 25 wherein the second bandwidth of each frequency spectrum is at least about 50% of the respective center frequency at points −6.8 dB with respect to the respective peak amplitude.

27. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for switching a plurality of voltages to form a bipolar transmit waveform; and a filter, responsive to the bipolar transmit waveform to suppress ultrasonic energy at the harmonic to form a filtered bipolar transmit waveform, said filtered bipolar transmit waveform characterized by a power level reduced by at least 30 dB at the harmonic as compared to the fundamental frequency.

28. The invention of claim 27 wherein the plurality of voltages comprise a positive voltage and a negative voltage.

29. The invention of claim 27 further comprising a voltage amplifier, responsive to the filtered bipolar transmit waveform.

30. The invention of claim 27 wherein the filter provides at least 10 dB suppression at the harmonic.

31. The invention of claim 27 wherein the filter comprises first and second filter sections, each filter section responsive to a respective unipolar component of the bipolar transmit waveform.

32. The invention of claim 27 wherein the power level is reduced by at least 40 dB at the harmonic as compared to the fundamental frequency.

33. The invention of claim 27 wherein the power level is reduced by at least 50 dB at the harmonic as compared to the fundamental frequency.

34. A method for ultrasonically imaging a target comprising the following steps:

(a) switching a plurality of DC voltages to form a bipolar transmit waveform:

(b) filtering the bipolar transmit waveform to form a filtered bipolar transmit waveform characterized by a fundamental and a harmonic frequency, said harmonic frequency reduced with respect to the fundamental frequency by at least 30 dB;

(c) transmitting ultrasonic energy into a target in response to the filtered bipolar transmit waveform; and (d) processing echo ultrasonic energy from the target at the harmonic for display.

35. The method of claim 34 wherein step (a) comprises the step of switching at least one positive DC voltage and at least one negative DC voltage to form the bipolar transmit waveform.

36. The method of claim 34 further comprising the step of amplifying the filtered bipolar transmit waveform prior to step (c).

37. The method of claim 35 wherein step (b) comprises the step of separately low pass filtering each unipolar component of the bipolar transmit waveform.

38. The method of claim 34 wherein power of the filtered bipolar transmit waveform at said harmonic frequency is reduced with respect to the fundamental frequency by at least 40 dB.

39. The method of claim 34 wherein power of the filtered bipolar transmit waveform at said harmonic frequency is reduced with respect to the fundamental frequency by at least 50 dB.

40. In a method for ultrasonically imaging a target, said method comprising the steps of (a) transmitting ultrasonic energy at a fundamental frequency, and (b) receiving reflected ultrasonic energy at a harmonic of the fundamental frequency, the improvement wherein step (a) comprises the step of:

(a1) filtering a transmit signal in a first mode of operation with a filter adapted to pass energy at the fundamental frequency and to suppress energy at the harmonic; and (a2) controlling a switch to selectively bypass the filtering step in a second mode of operation.

41. In an ultrasonic imaging system comprising a transducer, a transmitter coupled to the transducer and operative to transmit ultrasonic energy at a fundamental frequency, and a receiver responsive to ultrasonic energy at a harmonic of the fundamental frequency, the improvement comprising:

first and second signal paths coupled to the transmitter and the transducer;

a filter included in the first signal path, said filter adapted to suppress ultrasonic energy at the harmonic; and a switch coupled to the first and second signal paths, said switch operative to route signals from the transmitter to the transducer through a selectable one of the first and second signal paths.

42. The invention of claim 41 wherein the switch is disposed between the transmitter and the filter.

43. The invention of claim 41 wherein the switch is disposed between the filter and the transducer.

44. The invention of claim 41 wherein the switch is included in a multiplexer.

45. The invention of claim 41 further comprising an additional switch coupled to the first and second signal paths, wherein the first-mentioned and the additional switches are disposed on opposite sides of the filter.

46. The invention of claim 41 wherein at least one of the signal paths comprises an isolation circuit.

47. The invention of claim 41 further comprising means for automatically controlling the switch to select the first signal path during operation of the transmitter and to select the second path during operation of the receiver.

48. The invention of claim 41 wherein the second signal path comprises a second filter, said first-mentioned and second filters differing in filter characteristics.

49. A method for ultrasonically imaging a target comprising the following steps:
   (a) transmitting ultrasonic energy at a fundamental frequency along a plurality of transmit lines;
   (b) receiving ultrasonic energy at a harmonic of the fundamental frequency along a plurality of receive lines, wherein a plurality of said receive lines are formed in response to one of said transmit lines.

50. The method of claim 49 wherein the target comprises a added non-linear contrast agent.

51. A method for ultrasonically imaging a target, said method comprising the following steps:
   (a) transmitting ultrasonic energy at a fundamental frequency into the target in a transmit beam having a spread focus along an ultrasound line; and
   (b) receiving reflected ultrasonic energy from the target at a harmonic of the fundamental frequency.

52. The method of claim 50 wherein step (a) comprises transmitting the transmit beam having the ultrasonic energy uniformly focused along at least a portion of the ultrasound line.

53. A method for ultrasonically imaging- a target, said method comprising the following steps:
   (a) transmitting ultrasonic energy at a fundamental frequency into the target in a transmit beam having an axicon focus; and
   (b) receiving reflected ultrasonic energy from the target at a harmonic of the fundamental frequency.

54. The method of claim 53 wherein step (a) comprises transmitting the ultrasonic energy from a lens.

55. The method of claim 53 wherein step (a) comprises transmitting in the transmit beam having the axicon focus in an elevation dimension.

56. The method of claim 53 wherein step (a) comprises transmitting in the transmit beam having the axicon focus and an elevation dimension axicon focus.

57. A method for ultrasonically imaging a target, said method comprising the following steps:
   (a) transmitting ultrasonic energy at a fundamental frequency into the target in a transmit beam having a line focus, the line focus comprising a focal limit selected from the group consisting of: a near focal limit, an outer focal limit, and combinations thereof; and
   (b) receiving reflected ultrasonic energy from the target at a harmonic of the fundamental frequency.

58. The method of claim 57 wherein step (a) comprises transmitting in a transmit beam having a line focus comprising the near focal limit.

59. The method of claim 57 wherein step (a) comprises transmitting in a transmit beam having a line focus comprising the outer focal limit.

60. A method for ultrasonically imaging a target, said method comprising the following steps:
   (a) generating a transmit waveform such that ultrasonic power in the transmit waveform at a harmonic of a fundamental frequency is reduced by at least −30dB with respect to ultrasonic power in the transmit waveform at the fundamental frequency;
   (b) transmitting ultrasonic energy responsive to the transmit waveform into the target in a transmit beam having a line focus, and
   (c) receiving reflected ultrasonic energy from the target at a harmonic of the fundamental frequency.

61. A method for ultrasonically imaging a target, said method comprising the following steps:
   (a) transmitting ultrasonic energy at a fundamental frequency into the target in a transmit beam having at least two focal regions; and
   (b) receiving ultrasonic energy from the target at a harmonic of the fundamental frequency.

62. The method of claim 61 wherein said ultrasonic energy is transmitted in power bursts characterized by a power level at the harmonic which is reduced by at least 30 dB with respect to ultrasonic power in the power burst at the fundamental frequency.

63. The method of claim 61 wherein said target is free of contrast agent throughout an entire imaging session.

64. The method of claim 61 wherein said target comprises tissue and contrast agent.

65. The method of claim 61 wherein step (a) comprises spreading the beam.

66. The method of claim 61 wherein step (a) comprises multiple transmit zone firing.

67. The method of claim 61:
   further comprising (c) generating transmit waveforms as a function of a sampled envelope time domain signal; and
   wherein step (a) comprises transmitting the ultrasonic energy in response to the transmit waveforms.

68. The method of claim 67 wherein step (b) comprises receiving ultrasonic energy along four receive lines.

69. A method for ultrasonically imaging a target during an imaging session, said method comprising the following steps:
   (a) generating a transmit waveform characterized by a respective frequency spectrum having a respective center frequency, a respective peak amplitude, and a respective bandwidth, the bandwidth being at least about 30% of the respective center frequency at points −6.8 dB with respect to the respective peak amplitude, said frequency spectra reduced at a harmonic by more than 30 dB with respect to the peak amplitude
   (b) transmitting ultrasonic energy responsive to the transmit waveform at a fundamental frequency into a target, said target being free of contrast agent throughout the entire imaging session.
   (b) receiving ultrasonic energy from the target at the harmonic of the fundamental frequency.

70. The method of claim 69 wherein the bandwidth is at least about 50% of the respective center frequency at points −6.8 dB with respect to the respective peak amplitude.

71. The method of claim 69 or 70 wherein the frequency spectrum is reduced at the harmonic by at least about 50 dB with respect to the peak amplitude.

72. The method of claim 69 wherein step (a) comprises generating a voltage transmit waveform.

73. The method of claim 49 wherein step (b) comprises receiving ultrasonic energy along four receive lines.

74. The method of claim 49 wherein step (a) comprises transmitting the ultrasonic energy in defocused transmit beams.

* * * * *